US009265248B2

(12) United States Patent
Gentle et al.

(10) Patent No.: US 9,265,248 B2
(45) Date of Patent: Feb. 23, 2016

(54) WATER SOLUBLE ANTIMICROBIAL COMPOSITION

(75) Inventors: Thomas M. Gentle, St. Michael, MN (US); John J. Matta, Shoreview, MN (US); Adam W. Hauser, Minneapolis, MN (US); Wil Goetsch, Maple Grove, MN (US); Joshua Erickson, Champlin, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 14/238,930

(22) PCT Filed: Aug. 15, 2012

(86) PCT No.: PCT/US2012/050908
§ 371 (c)(1),
(2), (4) Date: Jun. 13, 2014

(87) PCT Pub. No.: WO2013/025783
PCT Pub. Date: Feb. 21, 2013

(65) Prior Publication Data
US 2014/0294749 A1    Oct. 2, 2014

Related U.S. Application Data

(60) Provisional application No. 61/523,701, filed on Aug. 15, 2011, provisional application No. 61/558,045, filed on Nov. 10, 2011.

(51) Int. Cl.
| | |
|---|---|
| A01N 25/22 | (2006.01) |
| A01N 47/40 | (2006.01) |
| A01N 43/16 | (2006.01) |
| A01N 31/08 | (2006.01) |
| A01N 31/14 | (2006.01) |
| A01N 31/16 | (2006.01) |
| A01N 43/80 | (2006.01) |
| A01N 55/02 | (2006.01) |
| A01N 55/00 | (2006.01) |
| A01N 33/12 | (2006.01) |
| A01N 25/10 | (2006.01) |
| A01N 25/34 | (2006.01) |
| D06M 13/463 | (2006.01) |
| D06M 16/00 | (2006.01) |

(52) U.S. Cl.
CPC ............... *A01N 25/22* (2013.01); *A01N 25/10* (2013.01); *A01N 25/34* (2013.01); *A01N 31/08* (2013.01); *A01N 31/14* (2013.01); *A01N 31/16* (2013.01); *A01N 33/12* (2013.01); *A01N 43/16* (2013.01); *A01N 43/80* (2013.01); *A01N 47/40* (2013.01); *A01N 55/00* (2013.01); *A01N 55/02* (2013.01); *D06M 13/463* (2013.01); *D06M 16/00* (2013.01)

(58) Field of Classification Search
CPC .... D06M 13/463; D06M 16/00; A01N 43/16; A01N 25/10; A01N 25/34; A01N 31/08; A01N 31/14; A01N 33/12; A01N 55/02; A01N 43/80; A01N 47/40; A01N 25/22; A01N 55/00
See application file for complete search history.

(56) References Cited

U.S. PATENT DOCUMENTS

| | | | |
|---|---|---|---|
| 5,505,953 A | 4/1996 | Chowhan | |
| 6,221,944 B1* | 4/2001 | Liebeskind et al. | 524/386 |
| 2005/0008534 A1 | 1/2005 | Hodge et al. | |
| 2007/0104766 A1* | 5/2007 | Wang et al. | 424/443 |
| 2008/0275230 A1 | 11/2008 | Liu et al. | |

FOREIGN PATENT DOCUMENTS

| | | |
|---|---|---|
| CN | 101461368 A | 6/2009 |
| EP | 0356264 A2 | 2/1990 |
| EP | 0492843 A2 | 7/1992 |
| KR | 2001078497 A | 8/2001 |
| WO | WO-98/44791 A1 | 10/1998 |
| WO | WO-01/01994 A1 | 1/2001 |
| WO | WO-01/97851 A2 | 12/2001 |
| WO | WO-02/30469 A2 | 4/2002 |
| WO | WO-02/069954 A2 | 9/2002 |
| WO | WO-03/070008 A1 | 8/2003 |
| WO | WO-2006/076334 A1 | 7/2006 |
| WO | WO-2006/081617 A1 | 8/2006 |
| WO | WO-2007/004067 A2 | 1/2007 |
| WO | WO-2007/027859 A1 | 3/2007 |
| WO | WO-2008/002434 A2 | 1/2008 |
| WO | WO-2009/108407 A1 | 9/2009 |
| WO | WO-2013/025783 A2 | 2/2013 |
| WO | WO-2013/025783 A3 | 2/2013 |

OTHER PUBLICATIONS

"International Application Serial No. PCT/US2012/050908, International Search Report mailed May 10, 2013", 9 pgs.
"International Application Serial No. PCT/US2012/050908, Invitation to Pay Additional Fees mailed Nov. 3, 2012", 11 pgs.
"International Application Serial No. PCT/US2012/050908, Written Opinion mailed May 10, 2013", 13 pgs.
Canadian Application Serial No. 2,844,791, Office Action mailed May 11, 2015, 3 pgs.

(Continued)

*Primary Examiner* — Anoop Singh
*Assistant Examiner* — Doan Phan
(74) *Attorney, Agent, or Firm* — Schwegman Lundberg & Woessner, P.A.

(57) ABSTRACT

The present invention provides for antimicrobial compositions, methods of preparing the antimicrobial compositions, methods of using the antimicrobial compositions, and/or kits that include the antimicrobial compositions. The antimicrobial compositions can be in a dry, solid (e.g., powdered) form, or can be in a liquid (e.g., aqueous) form.

18 Claims, 8 Drawing Sheets

(56) References Cited

OTHER PUBLICATIONS

Europeam Application Serial No. 12754132.4, Office Action mailed Apr. 4, 2014, 2 pgs.

International Application Serial No. PCT/US2012/050908, International Preliminary Report on Patentability mailed Feb. 27, 2014, 15 pgs.

* cited by examiner

WATER SOLUBLE ANTIMICROBIAL COMPOSITION

CLAIM OF PRIORITY

This application is a national stage application under 35 U.S.C. §371 of PCT/US2012/050908, filed Aug. 15, 2012, and published as WO 2013/025783 on Feb. 21, 2013, which claims the benefit of priority of U.S. Provisional Application No. 61/523,701, filed Aug. 15, 2011, entitled "WATER SOLUBLE ANTIMICROBAL POWDER," and claims the benefit of priority of U.S. Provisional Application No. 61/558,045, filed Nov. 10, 2011, entitled "WATER SOLUBLE ANTIMICROBAL POWDER," which applications and publication are incorporated by reference as if reproduced herein and made a part hereof in their entirety, and the benefit of priority of each of which is claimed herein.

BACKGROUND OF THE INVENTION

A variety of industries are subject to problems occurring with the growth of microorganisms. Such industries include, for example, the sporting equipment industry, the sporting apparel industry, the construction industry, medical healthcare institutions, the medical device industry, the lumber industry, and the textile industry. As such, reduction or elimination of microorganisms on surfaces is important in a broad variety of applications. One approach to interfere with the ability of microorganisms to survive on various materials is to modify the surface of those materials by attachment of antimicrobial agents.

Deciding how best to attach an antimicrobial agent to a material is guided, at least in part, by the planned end-use of the material. One important and useful consideration is that the antimicrobial activity be persistent. This may be achieved by permanently attaching the antimicrobial agent to the surface, so that it is unable to migrate or leach away from the modified material surface when the modified material is exposed to fluids. For example, for applications in which the modified material will come into contact with aqueous fluids, it is important that the antimicrobial agent is not rinsed away when the modified material comes into contact with aqueous fluids. For applications in which the modified material will come into contact with aqueous biological fluids, it is important that the antimicrobial agent is not rinsed away, or otherwise inactivated, when the modified material is exposed to aqueous biological fluids. For applications in which the modified material is to be used repeatedly, it is important that the antimicrobial agent is not washed or rinsed away when the modified material is washed or rinsed in fluids in between repeated uses.

One approach employs methods that attach silane-based quaternary ammonium compounds to particular substrates via a siloxane bond. For example, the AEGIS® product line includes products that utilize 3-(trimethoxysilyl)propyldimethyl octadecyl ammonium chloride. According to product literature, AEM 5700 includes 43% 3-trimethoxysilylpropyloctadecyl ammonium chloride in methanol, which can be used, e.g., to coat the surface of textiles. This is not a polymeric compound, although some interlinking of the applied silane may occur after application to the substrate. The methanol present in the commercial product AEM 5700 can be toxic, hazardous and therefore undesirable for some consumers. Another problem with the AEM liquid is the instability to pH change or temp/pressure changes. The product AEM 5700, upon removal of the methanol, will typically afford an oil or solid that is not readily soluble in water, and can degrade over time when exposed to ambient conditions.

The polymerized version of the AEM 5700 (Biosafe™) is a powder that is difficult to work with and leaves particulates behind upon dissolving in water. The Biosafe™, upon formulation into a sprayable liquid, includes an appreciable amount of undissolved solid particulates that should be removed (e.g., by filtering), or the sprayer can become clogged from the solid particulates. This can lead to costly and time-consuming steps in the production of liquid, sprayable commercial products manufactured from Biosafe™.

Consequently, there exists a need for antimicrobial compositions (e.g., ones that includes 3-(trimethoxysilyl)propyldimethyl octadecyl ammonium chloride), as well as methods of manufacturing the same in a convenient, reliable, and cost-effective manner.

SUMMARY OF THE INVENTION

The present invention provides for antimicrobial compositions, methods of preparing the antimicrobial compositions, methods of using the antimicrobial compositions, and/or kits that include the antimicrobial compositions. The antimicrobial compositions can be in a dry, solid (e.g., powdered) form, or can be in a liquid (e.g., aqueous) form.

In specific embodiments, the antimicrobial compositions described herein can effectively reduce the number of microbes located upon a substrate. In additional specific embodiments, the antimicrobial compositions described herein can effectively kill or inhibit a microorganism. In additional specific embodiments, the antimicrobial compositions described herein can effectively eliminate or lower the malodor associated with the growth of a microorganism. In additional specific embodiments, the antimicrobial compositions described herein can effectively eliminate or lower staining or discoloration of a substrate, which is associated with the growth of a microorganism. In additional specific embodiments, the antimicrobial compositions described herein are long-lasting, exhibiting antimicrobial activities for extended periods of time. This includes those embodiments in which the antimicrobial composition is formulated as a film or a coating on a substrate. In additional specific embodiments, the antimicrobial compositions described can employ antimicrobial agents that are relatively inexpensive, safe, non-toxic, and/or convenient to use. For example, the antimicrobial compositions can be applied to a substrate by spraying, dipping, laundering, soaking, brushing, and/or rolling the substrate with the antimicrobial composition.

In specific embodiments, the antimicrobial compositions described herein can effectively treat a textile, such as a moisture wicking performance fabric, without inhibiting the ability of the textile to wick away moisture from the user of the textile. In treating the textile, the antimicrobial composition can quickly kill microbes (e.g., bacteria, fungi, viruses, etc.) located on/in the textile, employing an alcohol (e.g., ethanol). Additionally, in specific embodiments, the antimicrobial composition can effectively prevent (or minimize) microbes from colonizing/growing on/in the textile, for extended periods of time (e.g., up to about 90 days).

In preventing (or minimizing) the microbes from colonizing/growing, the antimicrobial composition includes a polymeric carrier (e.g., polyvinyl alcohol) coated with an antimicrobial (e.g., 3-(trimethoxysilyl)propyl dimethyl octadecyl ammonium chloride), which effectively binds to the textile, providing the microbe protection without significantly reducing the effectiveness of wicking moisture. In not significantly reducing the effectiveness of wicking moisture, the treated textile will not be especially sensitive to detergents, cleaners, and antimicrobial products. As such, with use of the antimicrobial composition to treat a textile, the antimicrobial composition can improve the ability of the textile to wick away moisture from the user, while maintaining the antimicrobial properties. The antimicrobial composition will therefore have little or no negative impact on the wicking process for the treated textile, and in some instances will improve the moisture wicking performance, along with lasting antimicrobial effectiveness (e.g., up to about 90 days).

Suitable textiles include, e.g., polyester fabrics, synthetic polyester fabrics, non-engineered polyester fabrics, performance apparels, moisture wicking performance fabrics, delicate moisture wicking performance fabrics, and moisture wicking performance apparel.

The antimicrobial compositions described herein can be manufactured in a dry, solid (e.g., powdered) form, or can be manufactured in a liquid (e.g., aqueous) form. Manufacturers and consumers may prefer the solid form, as use of organic solvents such as methanol (which can be toxic, hazardous and therefore undesirable), are avoided. When manufactured in the solid form, the antimicrobial compositions described herein are relatively water-soluble.

Upon dissolving in water, the antimicrobial compositions described herein can include a relatively low amount of undissolved solid particulates. This will avoid the necessity of removing those solid particulates (e.g., by filtering) when formulating into a liquid, sprayable product. This will minimize the likelihood that the sprayer will become clogged from the solid particulates. The antimicrobial compositions described herein, both in a dry, solid (e.g., powdered) form, as well as the liquid (e.g., aqueous) form, are relatively stable to ambient conditions, and will undergo a relatively minimal amount of degradation over extended periods of time. The antimicrobial compositions will also retain the antimicrobial properties over extended periods of time. As such, the antimicrobial compositions can have a relatively extended shelf-life. Additionally, the antimicrobial compositions can avoid the necessity of being sealed in glass ampoules, which are typically employed for the extended periods of time related to the shipping and storage of some liquid antimicrobial compositions.

The present invention provides for an antimicrobial composition. The antimicrobial composition includes: (a) an antimicrobial agent, and (b) a polymeric carrier. The antimicrobial agent is relatively water soluble (e.g., has a solubility in water of at least about 0.05 g/mL at 80° C. and 1 atm). The polymeric carrier is also relatively water soluble (e.g., has a solubility in water of at least about 0.05 g/mL at 80° C. and 1 atm). Additionally, a significant portion of the antimicrobial agent is complexed with the polymeric carrier (e.g., at least about 20 mol. % of the antimicrobial agent is complexed with the polymeric carrier).

The present invention also provides for an antimicrobial composition that includes: (a) an antimicrobial agent that includes 3-(trimethoxysilyl)propyl dimethyl octadecyl ammonium chloride, and (b) a polymeric carrier that includes polyvinyl alcohol (PVA). The antimicrobial composition is essentially free of organic solvent (e.g., the antimicrobial composition includes less than about 0.1 wt. % organic solvent). In specific embodiments, the antimicrobial composition can be in the form of a dry, powdered composition. In additional specific embodiments, the antimicrobial agent can be a solid. In additional specific embodiments, the polymeric carrier can be a solid.

The present invention also provides for a method of preparing an antimicrobial composition. The method includes: (a) contacting an antimicrobial agent, a polymeric carrier and a solvent to form a slurry, and (b) removing the solvent from the slurry to form the antimicrobial composition. The antimicrobial agent is relatively water soluble (e.g., has a solubility in water of at least about 0.05 g/mL at 80° C. and 1 atm). The polymeric carrier is also relatively water soluble (e.g., has a solubility in water of at least about 0.05 g/mL at 80° C. and 1 atm). In specific embodiments, the antimicrobial composition can be in the form of a dry, powdered composition. In additional specific embodiments, the antimicrobial agent can be a solid. In additional specific embodiments, the polymeric carrier can be a solid.

The present invention also provides for a method of preparing an antimicrobial composition. The method includes: (a) contacting an antimicrobial agent that includes 3-(trimethoxysilyl)propyl dimethyl octadecyl ammonium chloride, a polymeric carrier that includes polyvinyl alcohol (PVA) and a solvent that includes hexanes, to form a slurry, and (b) removing in vacuum, at a temperature above about 25° C., the hexanes from the slurry to form the antimicrobial composition. The antimicrobial composition is essentially free of organic solvent (e.g., the antimicrobial composition includes less than about 0.1 wt. % organic solvent). A significant portion of the 3-(trimethoxysilyl)propyl dimethyl octadecyl ammonium chloride is complexed with the polyvinyl alcohol (PVA) (e.g., at least about 90 mol. % of the 3-(trimethoxysilyl)propyl dimethyl octadecyl ammonium chloride is complexed with the polyvinyl alcohol (PVA). Additionally, upon dissolving in water, the composition is essentially free of undissolved solid particulates (e.g., upon dissolving in water at 80° C. and 1 atm, the composition includes less than about 0.1 wt. % of undissolved solid particulates). In specific embodiments, the antimicrobial composition can be in the form of a dry, powdered composition. In additional specific embodiments, the antimicrobial agent can be a solid. In additional specific embodiments, the polymeric carrier can be a solid.

The present invention also provides for a method of preparing an aqueous antimicrobial composition. The method includes: (a) preparing an antimicrobial composition as described herein, and (b) dissolving the antimicrobial composition in an aqueous solution to provide the aqueous antimicrobial composition.

The present invention also provides for a liquid, aqueous antimicrobial composition. The composition includes: (a) an antimicrobial agent, (b) a polymeric carrier, and (c) water. The antimicrobial agent is relatively water soluble (e.g., has a solubility in water of at least about 0.05 g/mL at 80° C. and 1 atm). The polymeric carrier is also relatively water soluble (e.g., has a solubility in water of at least about 0.05 g/mL at 80° C. and 1 atm). Additionally, upon dissolving in water, the composition is essentially free of undissolved solid particulates (e.g., upon dissolving in water at 80° C. and 1 atm, the composition includes less than about 0.1 wt. % of undissolved solid particulates).

The present invention also provides for a liquid, aqueous antimicrobial composition. The liquid, aqueous antimicrobial composition includes: (a) an antimicrobial agent that includes 3-(trimethoxysilyl)propyl dimethyl octadecyl ammonium chloride, (b) a polymeric carrier that includes polyvinyl alcohol (PVA), (c) water, (d) alcohol, and (e) fragrance. Upon dissolving in water, the composition is essentially free of undissolved solid particulates (e.g., upon dissolving in water at 80° C. and 1 atm, the composition includes less than about 0.1 wt. % of undissolved solid particulates).

The present invention also provides for a liquid, aqueous antimicrobial composition. The liquid, aqueous antimicrobial composition includes: (a) about 0.01 to about 4.0 wt. % of 3-(trimethoxysilyl)propyl dimethyl octadecyl ammonium chloride (TPAC), (b) about 0.1 to about 4.0 wt. % of polyvinyl alcohol (PVA), (c) about 18 to about 99.9 wt. % water, (d) 0 to about 80.0 wt. % of ethanol, (e) 0 to about 2.0 wt. % fragrance, and (f) 0 to about 0.004 wt. % of an anti-foaming agent. Upon dissolving in water, the composition is essentially free of undissolved solid particulates (e.g., upon dissolving in water at 80° C. and 1 atm, the composition includes less than about 0.1 wt. % of undissolved solid particulates).

The present invention also provides for a liquid, aqueous antimicrobial composition. The liquid, aqueous antimicrobial composition includes: (a) about 0.5 wt. % of 3-(trimethoxysilyl)propyl dimethyl octadecyl ammonium chloride, (b) about 1.0 wt. % of polyvinyl alcohol (PVA), (c) about 88.3 wt. % of water, (d) about 10.0 wt. % of ethanol, (e) about 0.2 wt. % fragrance, and (f) about 0.002 wt. % of an anti-foaming agent. Upon dissolving in water, the composition is essentially free of undissolved solid particulates (e.g., upon dissolving in water at 80° C. and 1 atm, the composition includes less than about 0.1 wt. % of undissolved solid particulates).

The present invention also provides for a kit, that includes: (a) an enclosed container that includes a removable closure, (b) an antimicrobial composition described herein, located inside the enclosed container, and (c) printed indicia located on the enclosed container.

The present invention also provides for methods of using the antimicrobial compositions described herein. In specific embodiments, the antimicrobial compositions described herein can be used to effectively reduce the number of microbes located upon a substrate. In additional specific embodiments, the antimicrobial compositions described herein can be used to effectively kill or inhibit a microorganism. In additional specific embodiments, the antimicrobial compositions described herein can be used to effectively eliminate or lower the malodor associated with the growth of a microorganism. In additional specific embodiments, the antimicrobial compositions described herein can also be used to effectively eliminate or lower staining or discoloration of a substrate, which is associated with the growth of a microorganism.

DETAILED DESCRIPTION OF THE INVENTION

Figure 1:
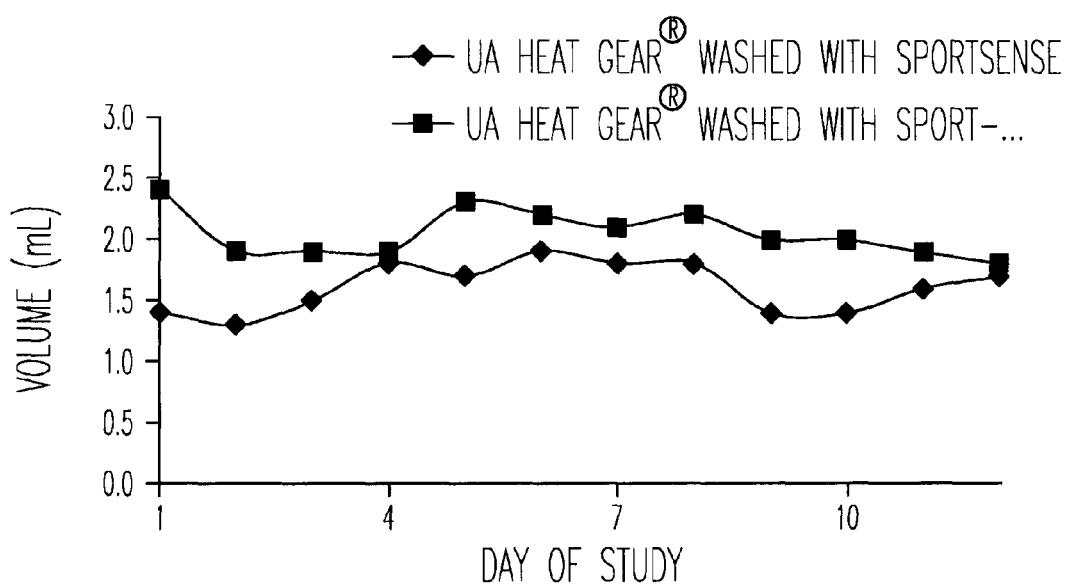
FIG. 1 illustrates a vertical fabric fluid dispersion for an exemplary composition of the present invention.
Figure 2:
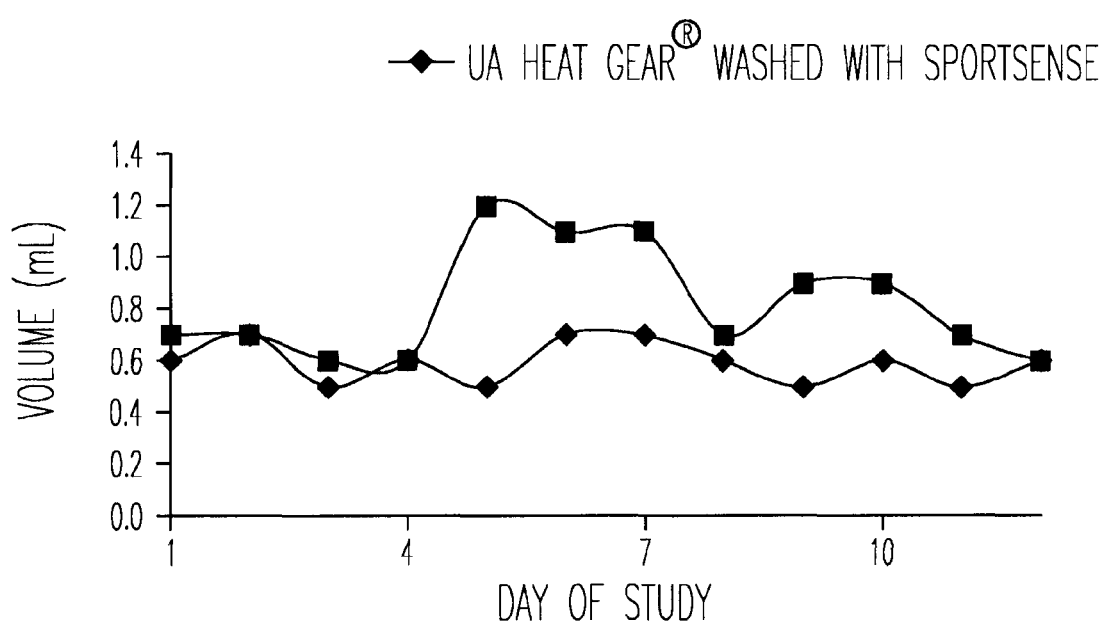
FIG. 2 illustrates a horizontal fabric fluid dispersion for an exemplary composition of the present invention.
Figure 3:
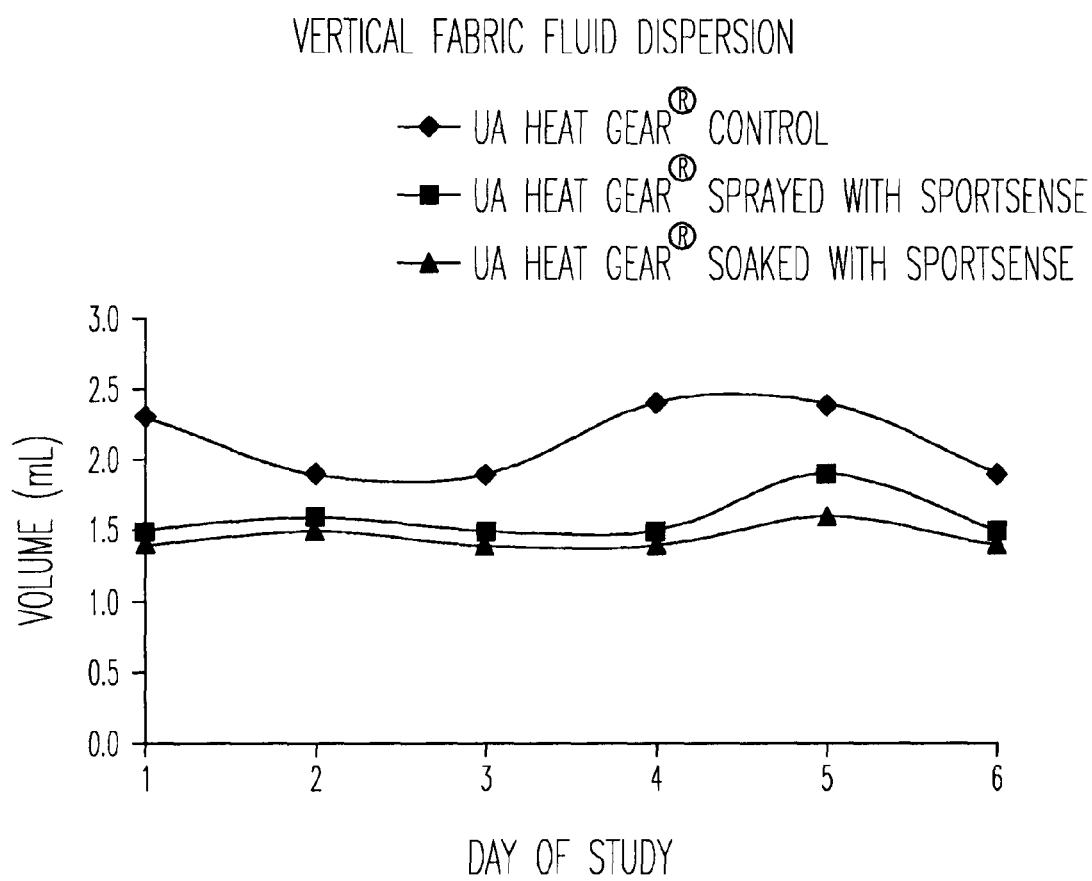
FIG. 3 illustrates a vertical fabric fluid dispersion for an exemplary composition of the present invention.
Figure 4:
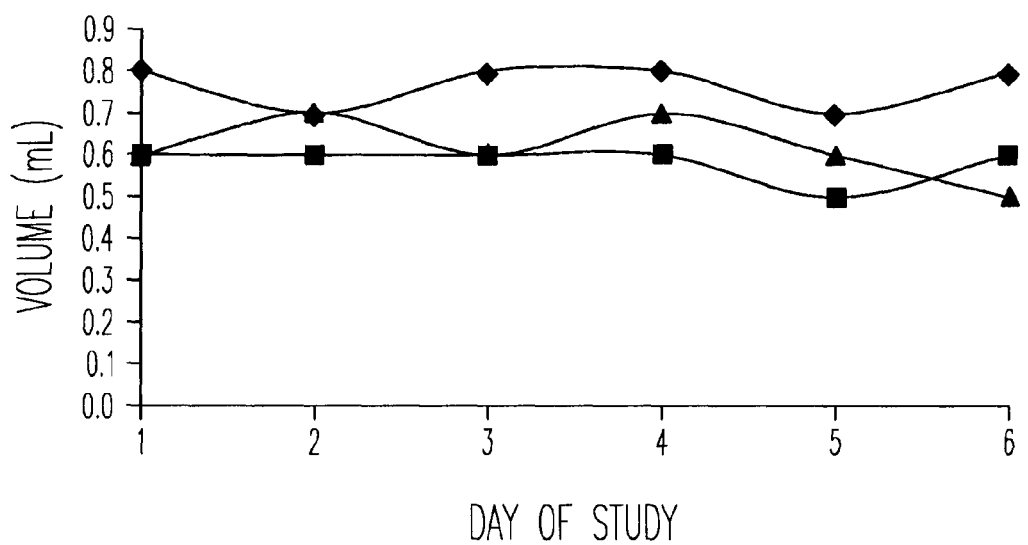
FIG. 4 illustrates a horizontal fabric fluid dispersion for an exemplary composition of the present invention.
Figure 5:
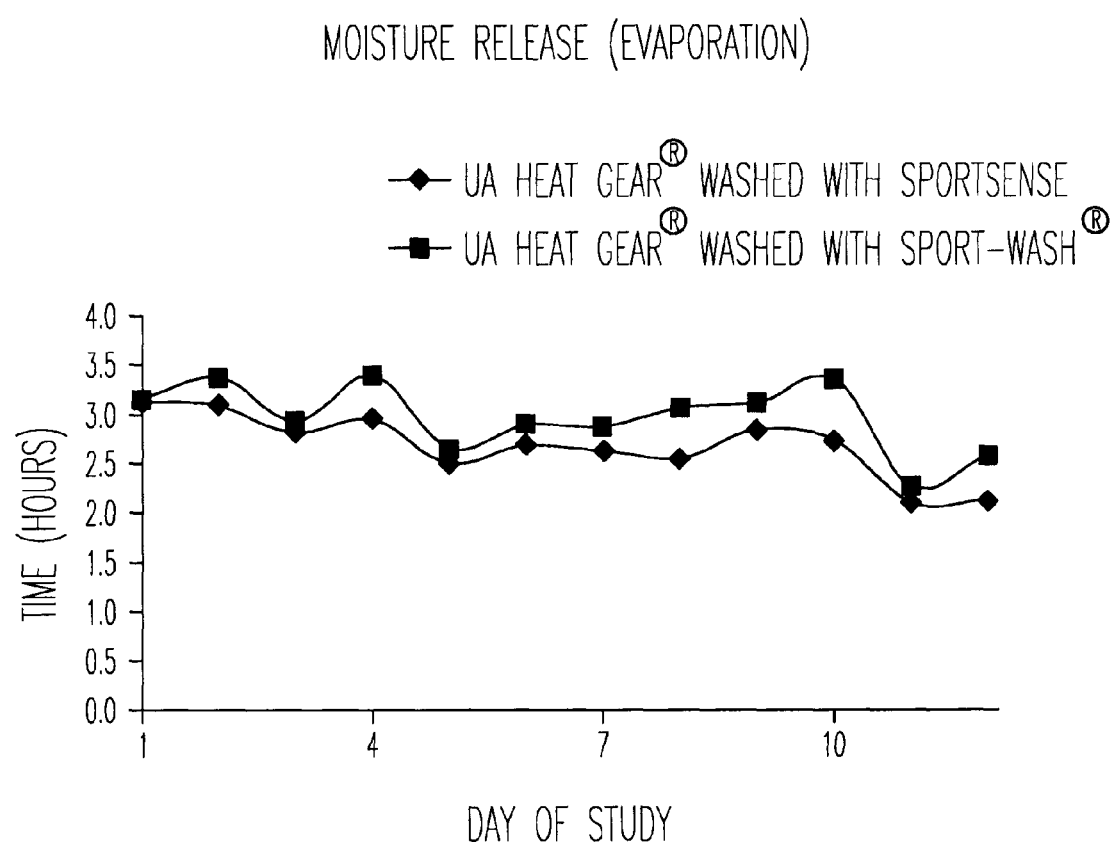
FIG. 5 illustrates a moisture release (evaporation) for an exemplary composition of the present invention.
Figure 6:
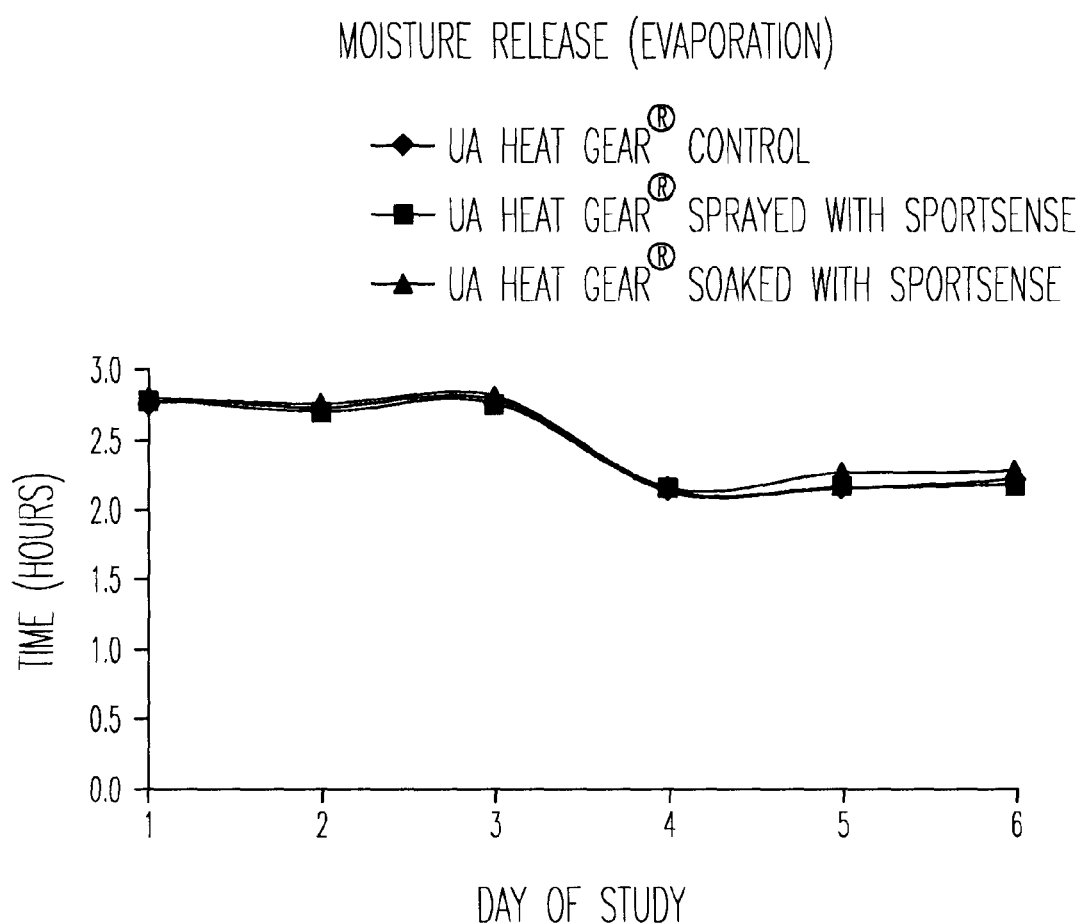
FIG. 6 illustrates a moisture release (evaporation) for an exemplary composition of the present invention.
Figure 7:
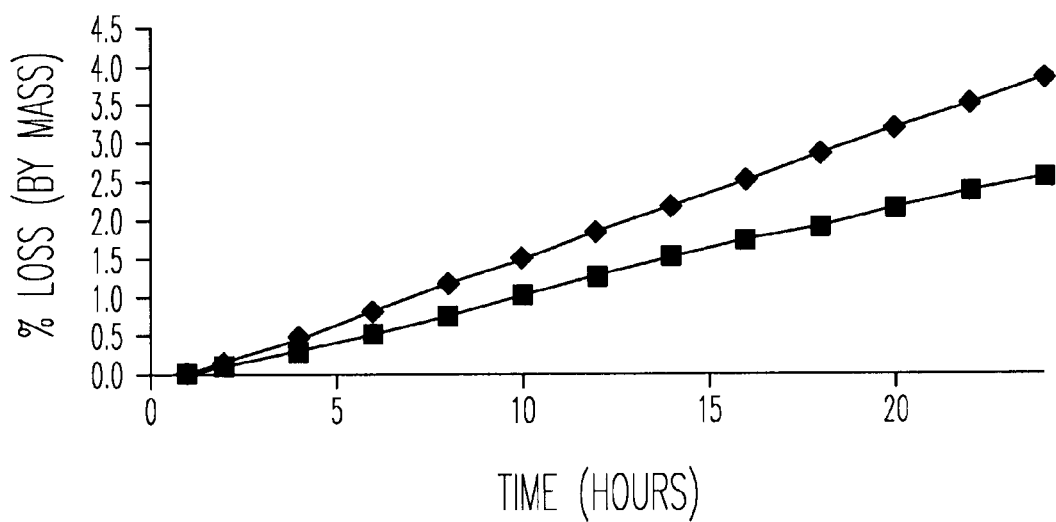
FIG. 7 illustrates a simulated perspiration test for an exemplary composition of the present invention.
Figure 8:
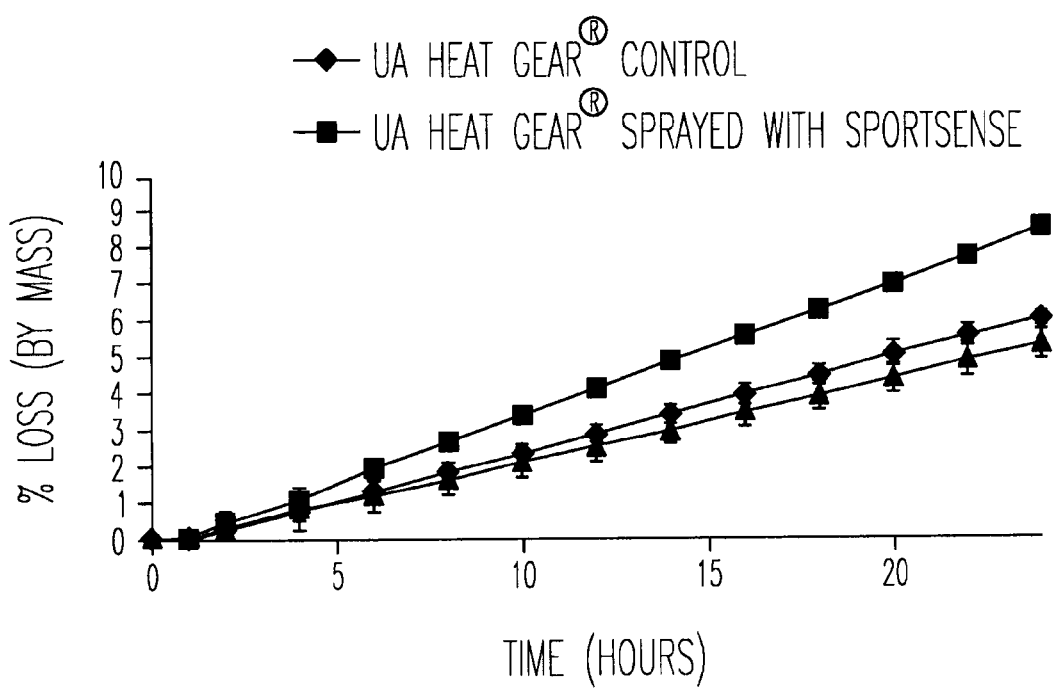
FIG. 8 illustrates a simulated perspiration test for an exemplary composition of the present invention.

Reference will now be made in detail to certain claims of the disclosed invention, examples of which are illustrated in the accompanying structures and formulas. While the disclosed subject matter will be described in conjunction with the enumerated claims, it will be understood that the disclosed subject matter is not intended to limit those claims. On the contrary, the disclosed subject matter is intended to cover all alternatives, modifications, and equivalents, which can be included within the scope of the present invention, as defined by the claims.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The present invention relates to antimicrobial compositions, methods of preparing the antimicrobial compositions, methods of using the antimicrobial compositions, and/or kits that include the antimicrobial compositions. When describing the present invention, the following terms have the following meanings, unless otherwise indicated.

Antimicrobial Composition

The antimicrobial composition described herein can be manufactured in a dry, solid (e.g., powdered) form, as well as the liquid (e.g., aqueous) form. When manufactured in the solid form, the antimicrobial compositions described herein be substantially free of liquid (e.g., can include less than about 1 wt. % liquid), yet can be can be relatively water-soluble. Additionally, manufacturers and consumers may prefer antimicrobial compositions in the solid form, as the use of organic solvents such as methanol (which can be toxic, hazardous and therefore undesirable), are avoided. Moreover, avoidance of liquid carriers will typically decrease the packaging, shipping and storage costs.

In specific embodiments, the dry, solid form antimicrobial composition car be used neat, in reducing the number of microbes located upon a substrate. For example, the dry, solid form antimicrobial composition can be directly applied to a substrate (e.g., carpet, rug or textile) under ambient conditions, for an extended period of time, sufficient to reduce the number of microbes located upon a substrate. In doing so, moisture from the atmosphere can assist the antimicrobial agent in sufficiently contacting the substrate. Alternatively, the dry, solid form antimicrobial composition can be used to manufacture a liquid form antimicrobial composition, which will itself reduce the number of microbes located upon a substrate. In such an embodiment, the dry, solid form antimicrobial composition can be used and viewed as an antimicrobial concentrate, or a concentrated form of antimicrobial composition.

In specific embodiments, the dry, solid form antimicrobial composition can be relatively water-soluble. Water solubility will help provide a suitable liquid composition in which the antimicrobial can effectively be delivered to the substrate. For example, the dry, solid form antimicrobial composition car have a solubility in water of at least about 0.05 g/mL at 80° C. and 1 atm, at least about 0075 g/mL at 80° C. and 1 atm, or at least about 0.1 g/mL at 80° C. and 1 atm.

Upon dissolving in water, the solid antimicrobial composition can include a relatively low amount of undissolved solid particulates. This will avoid the necessity of removing those solid particulates (e.g., by filtering) when formulating into a liquid, sprayable product. This will minimize the likelihood that the sprayer will become clogged from the solid particulates. For example, the dry, solid form antimicrobial composition, upon dissolving in water at 80° C. and 1 atm, can include less than about 1.0 wt. % of undissolved solid particulates, can include less than about 0.5 wt. % of undissolved solid particulates, can include less than about 0.1 wt. % of undissolved solid particulates, or can include less than about 0.01 wt. % of undissolved solid particulates.

As stated herein, the presence in commercial products of organic solvents such as methanol (which can be toxic and hazardous) are undesirable to some consumers. As such, the present invention provides for a dry, solid form antimicrobial composition that can be substantially free of organic solvents. For example, the dry, solid form antimicrobial composition can include less than about 1.0 wt. % organic solvent, less than about 0.5 wt. % organic solvent, less than about 0.1 wt. % organic solvent, or less than about 0.01 wt. % organic solvent. Such solvents include, e.g., organic solvents such as methanol.

The dry, solid form antimicrobial composition can remain relatively stable and retain the antimicrobial properties over extended periods of time. Such a stability and retention of antimicrobial properties will allow the commercial product to be shipped and stored over periods of time and conditions typically encountered with such products. For example, at least about 75 mol. % of the dry, solid form antimicrobial composition can remain stable and retain the antimicrobial properties at about 20° C. and at about 50% relative humidity, when exposed to the atmosphere, for at least about 9 months. Specifically, at least about 90 mol. % of the dry, solid form antimicrobial composition can remain stable and retain the antimicrobial properties at about 20° C. and at about 50% relative humidity, when exposed to the atmosphere, for at least about 3 months. More specifically, at least about 98 mol. % of the dry, solid form antimicrobial composition can remain stable and retain the antimicrobial properties at about 20° C. and at about 50% relative humidity, when exposed to the atmosphere, for at least about 9 months.

The dry, solid form antimicrobial composition can be relatively safe and non-toxic. Such a suitable safety profile will furnish a commercial product with a broader appeal to those consumers desiring a relatively safe and non-toxic product, when practical and feasible. For example, the dry, solid form antimicrobial composition can have a $LD_{50}$ in rats of greater than about 2 g/kg of body mass. Specifically, the dry, solid form antimicrobial composition can have a $LD_{50}$ in rats of greater than about 5 g/kg of body mass. More specifically, the dry, solid form antimicrobial composition can have a $LD_{50}$ in rats of greater than about 10 g/kg of body mass.

The dry, solid form antimicrobial composition can be a powder. Alternatively, the dry, solid form antimicrobial composition can be a film. Additionally, the dry, solid form antimicrobial composition can be relatively odorless and/or relatively colorless.

Antimicrobial Agent

The antimicrobial compositions described herein will include one or more antimicrobial agents. As used herein, an "antimicrobial agent" refers to a substance that kills a microorganism, inhibits the growth of a microorganism, or both. Typically, an antimicrobial kills a microorganism or inhibits their growth by cell wall damage, inhibition of cell wall synthesis, alteration of cell wall permeability, inhibition of the synthesis of proteins and nucleic acids, and inhibition of enzyme action. In specific embodiments, the antimicrobial agent is relatively inexpensive, safe, non-toxic, and/or convenient to use.

The antimicrobial agent can be a solid. Alternatively, the antimicrobial agent can be a liquid. Alternatively, the antimicrobial agent can be an oil.

The antimicrobial agent can be relatively water-soluble. Water solubility will help provide a suitable liquid composition in which the antimicrobial agent can effectively be delivered to the substrate. For example, the antimicrobial agent can have a solubility in water of at least about 0.05 g/mL at 80° C. and 1 atm, at least about 0.075 g/mL at 80° C. and 1 atm, or at least about 10 g/L at 20° C. and 1 atm at least about 0.1 g/mL at 80° C. and 1 atm.

The antimicrobial agent can be complexed with the polymeric carrier. For example, at least about 20 mol. % of the antimicrobial agent is complexed with the polymeric carrier, at least about 40 mol. % of the antimicrobial agent is complexed with the polymeric carrier, at least about 60 mol. % of the antimicrobial agent is complexed with the polymeric carrier, at least about 80 mol. % of the antimicrobial agent is complexed with the polymeric carrier, at least about 90 mol. % of the antimicrobial agent is complexed with the polymeric carrier, or at least about 95 mol. % of the antimicrobial agent is complexed with the polymeric carrier.

Any suitable antimicrobial agent can be employed, provided the antimicrobial agent effectively kills a microorganism, inhibits the growth of a microorganism, or both. Suitable specific classes of antimicrobial agents include, e.g., quaternary ammonium compound, a silver-containing compound, a phenol containing compound, a secondary or tertiary nitrogen containing compound, an aldehyde containing compound, a peroxygen containing compound.

Suitable specific antimicrobial agents include:

TPAC is 3-(trimethoxysilyl)propyl dimethyl octadecyl ammonium chloride. TPAC is also known as Dow Corning 5700 (DC 5700);

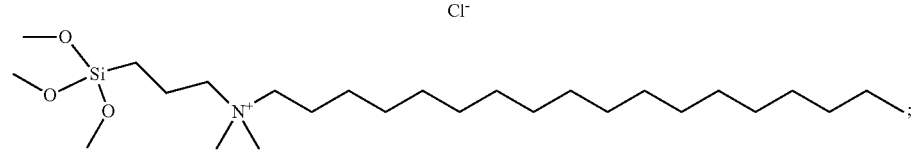 [SMILES: [Cl-] ; CCCCCCCCCCCCCCCCCC[N+](C)(C)CCC[Si](OC)(OC)OC]

poly(hexamethylene biguanide) hydrochloride (PHMB)

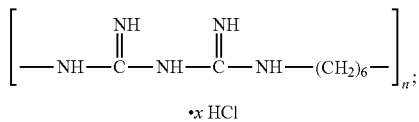

sialic acid (N-acetyl-neuraminic acid, Neu5Ac, NAN, NANA)

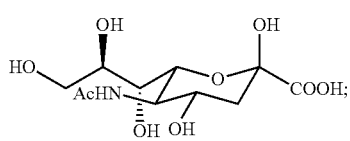 [SMILES: CC(=O)NC1C(O)CC(O)(C(=O)O)OC1[C@H](O)[C@H](O)CO]

poly(diallyldimethylammonium chloride) (poly DAD-MAC)

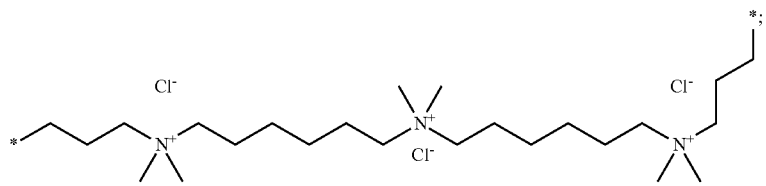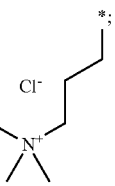

poly(vinyl benzyltrimethyl ammonium chloride) (PVBT-MAC);
5-chloro-2-(2,4-dichlorophenoxy)phenol;
alkyldimethylbenzylammonium chloride (ADBAC);
2,4,4'-trichloro-2'-hydroxydiphenyl ether

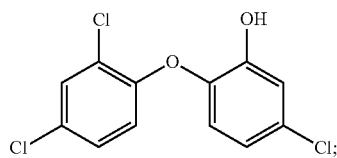 [SMILES: Oc1cc(Cl)ccc1Oc1ccc(Cl)cc1Cl]

methylisothiazolinone

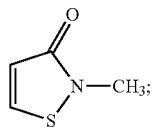

[N-(2-hydroxyl)propyl-3-trimethylammonium chitosan chloride] (HTCC); and
a silver complex of poly(amidoamine) (PAMAM);
2-isopropyl-5-methylphenol; and
Poly-D-glucosamine.

The antimicrobial agent can be employed in any suitable amount, provided the amount of antimicrobial agent is effective to kill a microorganism, inhibit the growth of a microorganism, or both. For example, the antimicrobial agent can be employed in up to about 10 wt. % of the liquid composition, in about 0.01 to about 10.0 wt. % of the liquid composition, in about 0.01 to about 5.0 wt. % of the liquid composition, or in about 0.1 to about 2.0 wt. % of the liquid composition. Specifically, the antimicrobial agent can be employed in up to about 80 wt. % of the antimicrobial composition, in about 0.1 to about 80.0 wt. % of the antimicrobial composition, in about 0.1 to about 50.0 wt. % of the antimicrobial composition, or in about 1 to about 50.0 wt. % of the antimicrobial composition.

The weight ratio of antimicrobial agent to polymeric carrier can be about 1:99 to about 99:1, about 1:10 to about 10:1, about 1:5 to about 5:1, or about 1:3 to about 3:1.

The antimicrobial agent can remain relatively stable and retain the antimicrobial properties over extended periods of time. Such a stability and retention of antimicrobial properties will allow the commercial product to be shipped and stored over periods of time and conditions typically encountered with such products. For example, at least about 75 mol. % of the antimicrobial agent can remain stable and retain the antimicrobial properties at about 20° C. and at about 50% relative humidity, when exposed to the atmosphere, for at least about 3 months. Specifically, at least about 90 mol. % of the antimicrobial agent can remain stable and retain the antimicrobial properties at about 20° C. and at about 50% relative humidity, when exposed to the atmosphere, for at least about 3 months. More specifically, at least about 98 mol. % of the antimicrobial agent can remain stable and retain the antimicrobial properties at about 20° C. and at about 50% relative humidity, when exposed to the atmosphere, for at least about 3 months.

The antimicrobial agent can be selected based at least in part upon the safety and toxicity. Such a suitable safety profile will furnish a commercial product with a broader appeal to those consumers desiring a relatively safe and non-toxic product, when practical and feasible. In such embodiments, the antimicrobial agent can be relatively safe and non-toxic. For example, the antimicrobial agent can have a $LD_{50}$ in rats of greater than about 2 g/kg of body mass. Specifically, the antimicrobial agent can have a $LD_{50}$ in rats of greater than about 5 g/kg of body mass. More specifically, the antimicrobial agent can have a $LD_{50}$ in rats of greater than about 10 g/kg of body mass.

Polymeric Carrier

The antimicrobial compositions described herein will include one or more polymeric carriers. As used herein, a "polymeric carrier" refers to a polymeric compound, or a mixture of polymeric compounds, that does not effectively dissolve in the solvent at 80° C. and 1 atm, does effectively dissolve in water at 80° C. and 1 atm, and sufficiently complexes a significant amount of antimicrobial agent when contacting with the solvent.

The polymeric carrier can be relatively water-soluble. Water solubility will help provide a suitable liquid composition in which the antimicrobial agent (which is complexed to the polymeric carrier) to be effectively be delivered to the substrate. For example, the polymeric carrier can have a solubility in water of at least about 0.05 g/mL at 80° C. and 1 atm, at least about 0.075 g/mL at 80° C. and 1 atm, or at least about 0.1 g/mL at 80° C. and 1 atm.

Any suitable polymeric carrier can be employed, provided the polymeric carrier does not effectively dissolve in the solvent at 80° C. and 1 atm, does effectively dissolve in water at 80° C. and 1 atm, and sufficiently complexes a significant amount of antimicrobial agent when contacting with the solvent. Suitable polymeric carriers include, e.g., polyvinyl acetate (PVAc), polyvinyl alcohol (PVA), starch (and modified/functionalized starches), polyethylene glycol (PEG), ethylene vinyl alcohol (EVA), cellulose, cellulose acetate, and chitosan.

The polymeric carrier does not effectively dissolve in the solvent at 80° C. and 1 atm. In specific embodiments, the polymeric carrier has a solubility in the solvent of less than about 1.0 g/L at 80° C. and 1 atm. In additional specific embodiments, the polymeric carrier has a solubility in the solvent of less than about 0.75 g/L at 80° C. and 1 atm. In additional specific embodiments, the polymeric carrier has a solubility in the solvent of less than about 0.5 g/L at 80° C. and 1 atm.

The polymeric carrier effectively dissolves in water at 80° C. and 1 atm. In specific embodiments, the polymeric carrier has a solubility in water of at least about 0.05 g/mL at 80° C. and 1 atm. In additional specific embodiments, the polymeric carrier has a solubility in water of at least about 0.075 g/mL at 80° C. and 1 atm. In additional specific embodiments, the polymeric carrier has a solubility in water of at least about 0.1 g/mL at 80° C. and 1 atm.

The polymeric carrier can be employed in any suitable amount, provided the amount of polymeric carrier does not effectively dissolve in the solvent at 80° C. and 1 atm, does effectively dissolve in water at 80° C. and 1 atm, and sufficiently complexes a significant amount of antimicrobial agent when contacting with the solvent. For example, the polymeric carrier can be employed in up to about 10 wt. % of the antimicrobial composition, in about 0.01 to about 10.0 wt. % of the antimicrobial composition, in about 0.1 to about 8.0 wt. % of the antimicrobial composition, or in about 0.1 to about 5.0 wt. % of the antimicrobial composition. Specifically, the polymeric carrier can be employed in up to about 80 wt. % of the antimicrobial composition. More specifically, the polymeric carrier can be employed in about 0.1 to about 80.0 wt. % of the antimicrobial composition. More specifically, the polymeric carrier can be employed in about 0.1 to about 50.0 wt. % of the antimicrobial composition. More specifically, the polymeric carrier can be employed in about 1 to about 50.0 wt. % of the antimicrobial composition.

The weight ratio of polymeric carrier to antimicrobial agent can be, e.g., about 1:99 to about 99:1, about 1:10 to about 10:1, about 1:5 to about 5:1, or about 3:1 to about 1:3.

Method of Preparing an Antimicrobial Composition

The present invention provides for methods of preparing an antimicrobial composition. The methods can include: (a) contacting an antimicrobial agent, a polymeric carrier and a solvent to form a slurry, and (b) removing the solvent from the slurry to form the antimicrobial composition. In specific embodiments, the antimicrobial composition can be in the form of a dry, powdered composition. In additional specific embodiments, the antimicrobial agent can be a solid. In additional specific embodiments, the polymeric carrier can be a solid.

Any suitable solvent can be employed, provided the solvent does not effectively dissolve the polymeric carrier at 80° C. and 1 atm, but does effectively dissolve the antimicrobial agent at 80° C. and 1 atm. As such, the polymeric carrier can be immiscible in the suitable solvent, and the antimicrobial agent can be miscible in the suitable solvent. One suitable class of suitable solvents includes non-polar aprotic organic solvents, e.g., hexanes. Another suitable class of suitable solvents includes polar aprotic organic solvents (e.g., chloroform) and polar protic organic solvents (e.g., ethanol). Additionally, the suitable solvent can include a single compound, or a mixture of two or more compounds.

The suitable solvent can also be selected based upon the ease, cost and efficiency of removing the solvent from the mixture of antimicrobial agent and polymeric carrier. For example, when the solvent is removed in vacuum, for example, at a temperature above about 25° C., a solvent that will have a sufficiently low boiling point (i.e., it is relatively volatile) can be used. Alternatively, the solvent can be removed via filtering or decanting the antimicrobial agent and polymeric carrier. In such embodiments, employing a solvent that will have a sufficiently low boiling point (i.e., it is relatively volatile) may not be particularly necessary.

The solvent can be employed in any suitable amount, provided the solvent does not effectively dissolve the polymeric carrier at 80° C. and 1 atm, does effectively dissolve the antimicrobial agent at 80° C. and 1 atm, and the solvent can subsequently be removed. For example, the solvent can be employed in about 1 milliliter (mL) per kilogram (kg) of polymeric carrier to about 10 liters (L) per gram (g) of polymeric carrier. Typically, the solvent can be employed in about 50 milliliter (mL) per kilogram (kg) of polymeric carrier, to about 2 liters (L) per gram (g) of polymeric carrier.

In specific embodiments, the methods of preparing the antimicrobial composition described herein can include: (a) contacting an antimicrobial agent that includes 3-(trimethoxysilyl)propyl dimethyl octadecyl ammonium chloride, a polymeric carrier that includes polyvinyl alcohol (PVA), and a solvent that includes hexanes, to form a slurry, and (h) removing the hexanes in vacuum from the slurry, at a temperature above about 25° C., to form the antimicrobial composition.

Additional specific embodiments include: (a) contacting antimicrobial agents that include alkyldimethylbezyl ammonium chloride and 3-(trimethoxysilyl)propyl dimethyl octadecyl ammonium chloride, a polymeric carrier that includes polyvinyl alcohol (PVA), and a solvent that includes ethanol, to form a slurry, and (h) removing the ethanol in vacuum from the slurry, at a temperature above about 25° C., to form the dry, powdered antimicrobial composition.

Without being bound to any particular theory, it is believed that upon formation of the antimicrobial composition, at least a portion of the antimicrobial agent becomes trapped by the polymer. As such, the antimicrobial agent does not necessarily adsorb or bind to the polymer, but is instead housed or trapped by the polymer.

Liquid, Aqueous Antimicrobial Composition

The liquid, aqueous antimicrobial compositions described herein can be relatively odorless and/or relatively colorless. Such physical properties can be desirable to some consumers, as the antimicrobial compositions will not have an offensive or unpleasant odor, nor will the antimicrobial compositions discolor or stain substrates such as clothing apparel.

The liquid, aqueous antimicrobial composition can include: (a) an antimicrobial agent (or agents), (b) a polymeric carrier (or carriers), and (c) water. In specific embodiments, the liquid, aqueous antimicrobial composition can include: (a) an antimicrobial agent that includes 3-(trimethoxysilyl)propyl dimethyl octadecyl ammonium chloride, (b) a polymeric carrier that includes polyvinyl alcohol (PVA), (c) water, (d) alcohol, and (e) fragrance. In further specific embodiments, the liquid, aqueous antimicrobial composition can include: (a) 3-(trimethoxysilyl)propyl dimethyl octadecyl ammonium chloride, (b) polyvinyl alcohol (PVA), (c) water, (d) alcohol, and (e) fragrance.

In specific embodiments, the liquid, aqueous antimicrobial composition can include: (a) antimicrobial agents that include 3-(trimethoxysilyl)propyl dimethyl octadecyl ammonium chloride and, alkyldimethylbezyl ammonium chloride (b) a polymeric carrier that includes polyvinyl alcohol (PVA), (c) water, (d) alcohol, and (e) fragrance.

In specific embodiments, the liquid, aqueous antimicrobial composition can include: (a) an antimicrobial agent that includes alkyldimethylbezyl ammonium chloride (b) a polymeric carrier that includes polyvinyl alcohol (PVA), (c) water, (d) buffer (e) and surfactant.

In further specific embodiments, the liquid, aqueous antimicrobial composition can include: (a) about 0.01 to about 4.0 wt. % of 3 (trimethoxysilyl)propyl dimethyl octadecyl ammonium chloride, (b) about 0.1 to about 4.0 wt. % of polyvinyl alcohol (PVA), (c) about 18 to about 99.9 wt. % water, (d) 0 to about 80.0 wt. % of ethanol, (e) 0 to about 2.0 wt % fragrance, and (f) 0 to about 0.004 wt. % of an anti-foaming agent. In further specific embodiments, the liquid, aqueous antimicrobial composition can include: (a) about 0.5 wt. % of 3 (trimethoxysilyl)propyl dimethyl octadecyl ammonium chloride, (b) about 1.0 wt. % of polyvinyl alcohol (PVA), (c) about 88.3 wt. % of water, (d) about 10.0 wt. % of ethanol, (e) about 0.2 wt. % fragrance, and (f) about 0.002 wt. % of an anti-foaming agent.

The liquid, aqueous antimicrobial composition can be essentially Free of undissolved solid particulates. For example, the liquid, aqueous antimicrobial composition can include less than about 1.0 wt. % of undissolved solid particulates, can include less than about 0.5 wt. % of undissolved solid particulates, can include less than about 0.1 wt. % of undissolved solid particulates, or can include less than about 0.01 wt. % of undissolved solid particulates. The inclusion of a minimal amount of undissolved solid particulates will avoid the necessity of removing those solid particulates (e.g., by filtering) when formulating into a liquid, sprayable product, which in turn, will minimize the likelihood that the sprayer will become clogged from the solid particulates.

The liquid, aqueous antimicrobial composition can be essentially free of heavy metals. For example, the liquid, aqueous antimicrobial composition can include less than about 0.5 wt. % of heavy metals, can include less than about 0.1 wt. % of heavy metals, can include less than about 0.01 wt. % of heavy metals, or can include less than about 0.001 wt. % of heavy metals.

The liquid, aqueous antimicrobial composition can be essentially free of poly-chlorinated phenols (PCPs). For example, the liquid, aqueous antimicrobial composition can include less than about 0.5 wt. % of poly-chlorinated phenols (PCPs), can include less than about 0.1 wt. % of poly-chlorinated phenols (PCPs), can include less than about 0.01 wt. % of poly-chlorinated phenols (PCPs), or can include less than about 0.001 wt. % of poly-chlorinated phenols (PCPs).

The liquid, aqueous antimicrobial composition can be essentially free of methanol. For example, the liquid, aqueous antimicrobial composition can include less than about 0.5 wt. % of methanol, can include less than about 0.1 wt. % of methanol, can include less than about 0.01 wt. % of methanol, or can include less than about 0.001 wt. % of methanol. The presence of organic solvents such as methanol (which can be toxic and hazardous) in commercial products can be undesirable to both manufacturers and consumers. As such, the avoidance of methanol in commercial products is preferred by some consumers and manufacturers.

The liquid, aqueous antimicrobial composition can remain relatively stable and retain the antimicrobial properties over extended periods of time. For example, at least about 75 mol. % of the liquid, aqueous antimicrobial composition can remain stable and retain the antimicrobial properties at about 20° C. and at about 50% relative humidity, when exposed to the atmosphere, for at least about 3 months. Specifically, at least about 90 mol. % of the liquid, aqueous antimicrobial composition can remain stable and retain the antimicrobial properties at about 20° C. and at about 50% relative humidity, when exposed to the atmosphere, for at least about 3 months. More specifically, at least about 98 mol. % of the liquid, aqueous antimicrobial composition can remain stable and retain the antimicrobial properties at about 20° C. and at about 50% relative humidity, when exposed to the atmosphere, for at least about 3 months.

The liquid, aqueous antimicrobial composition can be non-leaching. Additionally, the liquid, aqueous antimicrobial composition can be relatively safe and non-toxic. For example, the liquid, aqueous antimicrobial composition can have a $LD_{50}$ in rats of greater than about 1 ml/kg of body mass. Specifically, the liquid, aqueous antimicrobial composition can have a $LD_{50}$ in rats of greater than about 2 ml/kg of body mass. More specifically, the liquid, aqueous antimicrobial composition can have a $LD_{50}$ in rats of greater than about 5 ml/kg of body mass. More specifically, the liquid, aqueous antimicrobial composition can have a $LD_{50}$ in rats of greater than about 10 ml/kg of body mass.

The liquid, aqueous antimicrobial composition can be configured for use in a variety of types of liquid composition. For example, the aqueous antimicrobial composition can be configured for spraying, dipping, brushing, and/or rolling a substrate with the liquid antimicrobial composition. Additionally, the aqueous antimicrobial composition can be configured for use in a wide-variety of compositions. For example, the composition can be configured for use in manufacturing a plastic or rubber composition. Alternatively, the composition can be configured for use in manufacturing a fabric or textile composition. Specifically, the aqueous antimicrobial composition can be configured for use in an athletic equipment composition, an athletic gear composition, an athletic apparel composition, or an athletic footwear composition. More specifically, because the composition can readily be configured for use in a sprayable composition, the aqueous antimicrobial composition can be configured for use in a sprayable athletic equipment composition, a sprayable athletic gear composition, a sprayable athletic apparel composition, or a sprayable athletic footwear composition.

In specific embodiments, the liquid, aqueous antimicrobial compositions can improve the ability of specified textiles to wick away moisture from the user of the textile. For example, when applied to a textile that includes polyester, the liquid, aqueous antimicrobial compositions can improve the ability of the polyester to wick away moisture from the user.

Method of Preparing an Aqueous Antimicrobial Composition

As stated herein, the dry, solid form antimicrobial composition can be used to manufacture a liquid form antimicrobial composition. Methods of preparing the aqueous antimicrobial composition can include: (a) preparing a dry, solid form antimicrobial composition as described herein, and (b) dissolving the dry, solid form antimicrobial composition in an aqueous solution to provide the aqueous antimicrobial composition.

The methods of preparing aqueous antimicrobial compositions described herein provide aqueous antimicrobial compositions that can be essentially free of undissolved solid particulates. This will avoid the necessity of removing those solid particulates (e.g., by filtering) when formulating into a liquid, sprayable product. This will minimize the likelihood that the sprayer will become clogged from the solid particulates.

Methods of Using the Aqueous Antimicrobial Composition

The aqueous antimicrobial compositions can be used in a wide-variety of applications or uses. Typically, the aqueous antimicrobial compositions will be used to reduce the number of microbes located upon a substrate. For example, the aqueous antimicrobial compositions can be used to kill or inhibit a microorganism, can be used to eliminate or lower malodor associated with the growth of a microorganism, and/or can be used to eliminate or lower staining or discoloration of a substrate. The use of the aqueous antimicrobial compositions will typically include contacting a topical surface of a substrate with an effective amount of the aqueous antimicrobial composition, for a sufficient period of time.

The aqueous antimicrobial compositions can be applied to a wide-variety of substrates. For example, the aqueous antimicrobial compositions can be applied to a topical surface of a mammal, non-woven fabric, woven fabric, natural textile, synthetic textile, organic particulate, inorganic particulate, fiber, agglomerate, foam, film, cellulosic material, metal, plastic, natural rubber, synthetic rubber, glass, paint, stain, adhesive, stone, grout, fiberglass, medical device, clothing apparel, sporting equipment, wood, concrete, construction product, building product, and/or activated carbon. Suitable textiles include, e.g., polyester fabrics, synthetic polyester fabrics, non-engineered polyester fabrics, performance apparels, moisture wicking performance fabrics, delicate moisture wicking performance fabrics, and moisture wicking performance apparel. One suitable line of performance apparels is commercially sold under the Under Armour® label.

In specific embodiments, the aqueous antimicrobial composition can be directly applied to a substrate, such as a textile (e.g., clothing apparel, such as a shirt or socks) or sporting equipment (e.g., hockey gloves or pads). In such embodiments, upon application, the liquid in the composition will essentially evaporate, leaving the antimicrobial agent and polymeric carrier remaining on the substrate. The antimicrobial agent can remain relatively stable and retain the antimicrobial properties over extended periods of time typically encountered with the specific use of the aqueous antimicrobial compositions. Factors such as frequency and duration of using the substrate, frequency and duration of washing or laundering the substrate, as well as frequency and duration of exposure to sunlight and harsh chemicals will influence both the stability of the antimicrobial agent as well as the retention of the antimicrobial properties, over the extended periods of time.

In specific embodiments, the aqueous antimicrobial compositions can be applied to a substrate, such as a moisture wicking performance fabric. After exposing the fabric to the aqueous antimicrobial composition, the alcohol (e.g., ethanol) will quickly kill odor causing bacteria and will typically evaporate along with water. During the evaporation of fluid, the polymeric carrier (e.g., polyvinyl alcohol), being relatively vapor permeable, will allow moisture to pass through the fabric without being significantly hindered.

In specific embodiments, the aqueous antimicrobial compositions can be applied to a substrate, thereby providing a coating or film on the substrate. The coating or film can provide antimicrobial properties to the substrate (e.g., can effectively kill or inhibit a microorganism, can effectively eliminate or lower malodor associated with the growth of a microorganism, and/or can effectively eliminate or lower staining or discoloration of a substrate). When the aqueous antimicrobial compositions are applied to a substrate to provide a coating or film on the substrate, the resulting film or coating can remain relatively stable and retain the antimicrobial properties over extended periods of time. For example, the coating or film can remain stable and retain the antimicrobial properties for at least about 1 year. In specific embodiments, the coating or film can remain stable and retain the antimicrobial properties for about 1 to about 5 years. In additional specific embodiments, the coating or film can remain stable and retain the antimicrobial properties for about 1 to about 10 years. In additional specific embodiments, the coating or film can remain stable and retain the antimicrobial properties for about 1 to about 15 years. Depending on the constituents and how the composition is made, the longevity of the films can vary drastically.

As such, liquid antimicrobial compositions described herein can be long-lasting, exhibiting antimicrobial activities for extended periods of time. This includes those embodiments in which the liquid antimicrobial composition is formulated as a film or a coating on a substrate, as well as those in which the substrate is treated one or more times with the antimicrobial compositions.

In specific embodiments, the microorganism can include at least one of a virus, fungus, mold, algae, yeast, mushroom and bacterium.

As used herein, "fungi" or "fungus" refers to a large and diverse group of eucaryotic microorganisms whose cells contain a nucleus, vacuoles, and mitochondria. Fungi include algae, molds, yeasts, mushrooms, and slime molds. See, Biology of Microorganisms, T. Brock and M. Madigan, 6th Ed., 1991, Prentice Hill (Englewood Cliffs, N.J.). Exemplary fungi include Ascomycetes (e.g., *Neurospora, Saccharomyces, Morchella*), Basidiomycetes (e.g., *Amanita, Agaricus*), Zygomycetes (e.g., *Mucor, Rhizopus*), Oomycetes (e.g., *Allomyces*), and Deuteromycetes (e.g., *Penicillium, Aspergillus*).

As used herein, "algae" refers to a large and diverse assemblage of eucaryotic organisms that contain chlorophyll and carry out oxygenic photosynthesis. See, Biology of Microorganisms, T. Brock and M. Madigan, 6th Ed., 1991, Prentice Hill (Englewood Cliffs, N.J.). Exemplary algae include Green Algae (e.g., *Chlamydomonas*), Euglenids (e.g., *Euglena*), Golden Brown Algae (e.g., *Navicula*), Brown Algae (e.g., *Laminaria*), Dinoflagellates (e.g., *Gonyaulax*), and Red Algae (e.g., *polisiphonia*).

As used herein, "mold" refers to a filamentous fungus, generally a circular colony that may be cottony, wooly, etc. or glabrous, but with filaments not organized into large fruiting bodies, such as mushrooms. See, e.g., Stedman's Medical Dictionary, 25th Ed., Williams & Wilkins, 1990 (Baltimore, Md.). One exemplary mold is the Basidiomycetes called wood-rotting fungi. Two types of wood-rotting fungi are the white rot and the brown rot. An ecological activity of many fungi, especially members of the Basidiomycetes is the decomposition of wood, paper, cloth, and other products derived from natural sources. Basidiomycetes that attack these products are able to utilize cellulose or lignin as carbon and energy sources. Lignin is a complex polymer in which the building blocks are phenolic compounds. It is an important constituent of woody plants. The decomposition of lignin in nature occurs almost exclusively through the agency of these wood-rotting fungi. Brown rot attacks and decomposes the cellulose and the lignin is left unchanged. White rot attacks and decomposes both cellulose and lignin. See, Biology of Microorganisms, T. Brock and M. Madigan, 6th Ed., 1991, Prentice Hill (Englewood Cliffs, N.J.).

As used herein, "yeast" refers to unicellular fungi, most of which are classified with the Ascomytes. See, Biology of Microorganisms, T. Brock and M. Madigan, 6th Ed., 1991, Prentice Hill (Englewood Cliffs, N.J.).

As used herein, "mushrooms" refer to filamentous fungi that are typically from large structures called fruiting bodies, the edible part of the mushroom. See, Biology of Microorganisms, T. Brock and M. Madigan, 6th Ed., 1991, Prentice Hill (Englewood Cliffs, N.J.).

As used herein, "slime molds" refers to nonphototrophic eucaryotic microorganisms that have some similarity to both fungi and protozoa. The slime molds can be divided into two groups, the cellular slime molds, whose vegetative forms are composed of single amoeba-like cells, and the acellular slime molds, whose vegetative forms are naked masses of protoplasms of indefinite size and shape called plasmodia. Slime molds live primarily on decaying plant matter, such as wood, paper, and cloth. See, Biology of Microorganisms, T. Brock and M. Madigan, 6th Ed., 1991, Prentice Hill (Englewood Cliffs, N.J.).

As used herein, a "virus" refers to a small infectious agent that can replicate only inside the living cells of organisms. Virus particles (known as virions) consist of two or three parts: the genetic material made from either DNA or RNA, long molecules that carry genetic information; a protein coat that protects these genes; and in some cases an envelope of lipids that surrounds the protein coat when they are outside a cell. The shapes of viruses range from simple helical and icosahedral forms to more complex structures. The average virus is about one one-hundredth the size of the average bacterium. An enormous variety of genomic structures can be seen among viral species; as a group they contain more structural genomic diversity than plants, animals, archaea, or bacteria. There are millions of different types of viruses, although only about 5,000 of them have been described in detail. A virus has either DNA or RNA genes and is called a DNA virus or a RNA virus respectively. The vast majority of viruses have RNA genomes. Plant viruses tend to have single-stranded RNA genomes and bacteriophages tend to have double-stranded DNA genomes.

Kits

The present invention provides for a kit that includes: (a) an enclosed container that includes a removable closure, (h) an antimicrobial composition as described herein, located inside the enclosed container, and (c) printed indicia located on the enclosed container.

The kit can include a liquid applicator that includes at least one of a spray bottle, wipe, cloth, sponge, non-woven fabric, and woven fabric.

Specific enumerated embodiments [1] to [66] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

Enumerated Embodiments

[1.] The present invention provides for an antimicrobial composition that includes:
 (a) an antimicrobial agent, and
 (b) a polymeric carrier,
wherein,
 the antimicrobial agent has a solubility in water of at least about 0.05 g/mL at 80° C. and 1 atm,
 the polymeric carrier has a solubility in water of at least about 0.05 g/mL at 80° C. and 1 atm, and
 at least about 20 mol. % of the antimicrobial agent is complexed with the polymeric carrier.

[2.] The present invention also provides for the antimicrobial composition of embodiment 1, having a solubility in water of at least about 0.05 g/mL at 80° C. and 1 atm.

[3.] The present invention also provides for the antimicrobial composition of embodiment 1, wherein upon dissolving in water at 80° C. and 1 atm, includes less than about 0.1 wt. % of undissolved solid particulates.

[4.] The present invention also provides for the antimicrobial composition of any one of embodiments 1-3, including less than about 0.1 wt. % organic solvent.

[5.] The present invention also provides for the antimicrobial composition of any one of embodiments 1-3, including less than about 0.1 wt. % methanol.

[6.] The present invention also provides for the antimicrobial composition of any one of embodiments 1-5, wherein at least about 95 mol. % of the antimicrobial agent is complexed with the polymeric carrier.

[7.] The present invention also provides for the antimicrobial composition of any one of embodiments 1-6, wherein at least about 90 mol. % of antimicrobial composition will remain stable at about 20° C. and at about 50% relative humidity, when exposed to the atmosphere, for at least about 3 months.

[8.] The present invention also provides for the antimicrobial composition of any one of embodiments 1-7, that is relatively non-toxic, such that the $LD_{50}$ in rats is greater than about 2 g/kg of body mass.

[9.] The present invention also provides for the antimicrobial composition of any one of embodiments 1-8, wherein the antimicrobial agent is a solid.

[10.] The present invention also provides for the antimicrobial composition of any one of embodiments 1-8, wherein the antimicrobial agent is a liquid.

[11.] The present invention also provides for the antimicrobial composition of any one of embodiments 1-10, wherein the antimicrobial agent includes at least one of a quaternary ammonium compound; a silver-containing compound, a phenol containing compound, a secondary or tertiary nitrogen containing compound, an aldehyde containing compound, and a peroxygen containing compound.

[12.] The present invention also provides for the antimicrobial composition of any one of embodiments 1-10, wherein the antimicrobial agent includes at least one of:

3-(trimethoxysilyl)propyl dimethyl octadecyl ammonium chloride

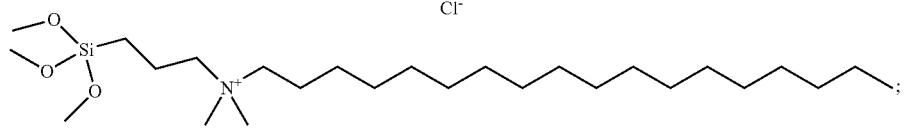 [SMILES: [Cl-] ; CCCCCCCCCCCCCCCCCC[N+](C)(C)CCC[Si](OC)(OC)OC]

poly(hexamethylene biguanide) hydrochloride (PHMB)

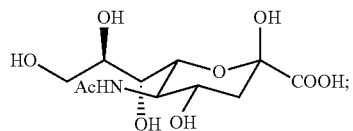 [SMILES: CC(=O)NC1C(O)CC(O)(C(=O)O)OC1[C@H](O)[C@H](O)CO]

poly(diallyldimethylammonium chloride) (poly DADMAC)

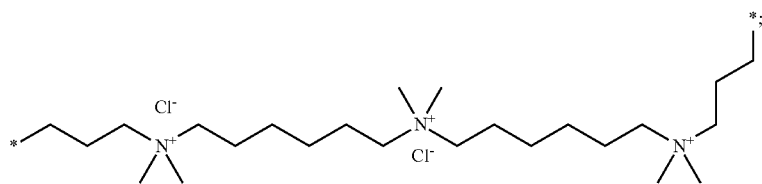

poly(vinyl benzyltrimethyl ammonium chloride) (PVBT-MAC);
5-chloro-2-(2,4-dichlorophenoxy)phenol;
alkyldimethylbenzylammonium chloride (ADBAC);
2,4,4'-trichloro-2'-hydroxydiphenyl ether

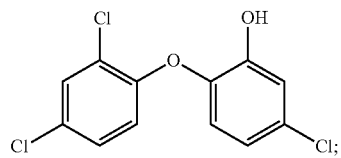 [SMILES: Oc1cc(Cl)ccc1Oc1ccc(Cl)cc1Cl]

methylisothiazolinone

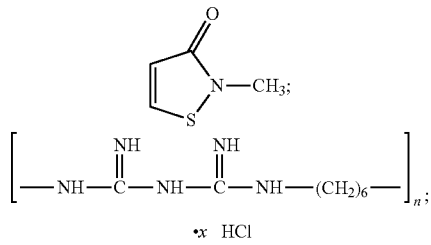

sialic acid (N-acetyl-neuraminic acid, Neu5Ac, NAN, NANA);
[N-(2-hydroxyl)propyl-3-trimethylammonium chitosan chloride] (HTCC); and
a silver complex of poly(amidoamine) (PAMAM);
2-isopropyl-5-methylphenol;
Chitosan and
poly-D-glucosamine.

[13.] The present invention also provides for the antimicrobial composition of any one of embodiments 1-12, wherein the polymeric carrier is a solid.

[14.] The present invention also provides for the antimicrobial composition of any one of embodiments 1-12, wherein the polymeric carrier includes at least one of polyvinyl acetate (PVAc), polyvinyl alcohol (PVA), starch, polyethylene glycol (PEG), ethylene vinyl alcohol (EVA), cellulose, cellulose acetate, and chitosan.

[15.] The present invention also provides for the antimicrobial composition of any one of embodiments 1-14, wherein the weight ratio of antimicrobial agent to polymeric carrier is about 1:99 to about 99:1.

[16.] The present invention also provides for the antimicrobial composition of any one of embodiments 145, wherein the antimicrobial composition is in a dry, solid form.

[17.] The present invention also provides for the antimicrobial composition of any one of embodiments 1-15, wherein the antimicrobial composition is a powder.

[18.] The present invention also provides for the antimicrobial composition of any one of embodiments 1-15, wherein the antimicrobial composition is a film.

[19.] The present invention also provides for the antimicrobial composition of any one of embodiments 1-15, wherein the antimicrobial composition is an antimicrobial concentrate.

[20.] The present invention also provides for the antimicrobial composition of any one of embodiments 1-19, wherein the antimicrobial composition is relatively odorless.

[21.] The present invention also provides for the antimicrobial composition of any one of embodiments 1-20, wherein the antimicrobial composition is relatively colorless.

[22.] The present invention also provides for an antimicrobial composition including:
(a) an antimicrobial agent including 3-(trimethoxysilyl)propyl dimethyl octadecyl ammonium chloride, and
(b) a polymeric carrier including polyvinyl alcohol (PVA), wherein the antimicrobial composition includes less than about 0.1 wt. % organic solvent.

[23.] The present invention also provides for the antimicrobial composition of embodiment 22, which is powdered and wherein upon dissolving in water at 80° C. and 1 atm, the composition includes less than about 0.1 wt. % of undissolved solid particulates,

[24.] The present invention also provides for the antimicrobial composition of and one of embodiments 22-23, wherein at least about 90 mol. % of the 3-(trimethoxysilyl)propyl dimethyl octadecyl ammonium chloride is complexed with the polyvinyl alcohol (PVA).

[25.] The present invention also provides for a method of preparing an antimicrobial composition of any one of embodiments 1-24, the method including:
(a) contacting an antimicrobial agent, a polymeric carrier and a solvent to form a slurry, and
(b) removing the solvent from the slurry to form the antimicrobial composition,
wherein,
the antimicrobial agent has a solubility in water of at least about 0.05 g/mL at 80° C. and 1 atm, and a solubility in the solvent of at least about 0.1 g/L at 80° C. and 1 atm, and
the polymeric carrier has a solubility in water of at least about 0.05 g/mL at 80° C. and 1 atm, and a solubility in the solvent of less than about 1.0 g/mL at 80° C. and 1 atm.

[26.] The present invention also provides for the method of embodiment 25, wherein the solvent includes a non-polar aprotic organic solvent.

[27.] The present invention also provides for the method of any one of embodiments 25-26, wherein the solvent includes hexanes.

[28.] The present invention also provides for the method of any one of embodiments 25-27, wherein the solvent is removed in vacuum.

[29.] The present invention also provides for the method of any one of embodiments 25-27, wherein the solvent is removed by filtration.

[30.] The present invention also provides for the method of any one of embodiments 25-29, wherein the solvent is removed at a temperature above about 25° C.

[31.] The present invention also provides for a method of preparing an antimicrobial composition, the method including:

(a) contacting an antimicrobial agent including 3-(trimethoxysilyl)propyl dimethyl octadecyl ammonium chloride, a polymeric carrier including polyvinyl alcohol (PVA) and a solvent including hexanes to form a slurry, and (b) removing in vacuum, at a temperature above about 25° C., the hexanes from the slurry to form the dry, powdered antimicrobial composition, including less than about 0.1 wt. % organic solvent, wherein, at least about 20 mol. % of the 3-(trimethoxysilyl)propyl dimethyl octadecyl ammonium chloride is complexed with the polyvinyl alcohol (PVA), and upon dissolving in water at 80° C. and 1 atm, the composition includes less than about 0.1 wt. % of undissolved solid particulates.

[32.] The present invention also provides for a method of preparing an aqueous antimicrobial composition, the method including:

(a) preparing an antimicrobial composition of any one of embodiments 23-29, and (b) dissolving the antimicrobial composition in an aqueous solution to provide the aqueous antimicrobial composition.

[33.] The present invention also provides for the method of embodiment 32, wherein the aqueous antimicrobial composition includes less than about 0.1 wt. % of undissolved solid particulates.

[34.] The present invention also provides for the method of embodiment 32, wherein the aqueous antimicrobial composition includes less than about 0.1 wt. % of undissolved solid particulates, such that the method of preparing the aqueous antimicrobial composition does not include filtering the aqueous antimicrobial composition to remove undissolved solid particulates.

[35.] The present invention also provides for a liquid, aqueous antimicrobial composition including:

(a) an antimicrobial agent, (b) a polymeric carrier, and (c) water, which includes less than about 0.1 wt. % of undissolved solid particulates, wherein, the antimicrobial agent has a solubility in water of at least about 0.05 g/mL at 80° C. and 1 atm, and the polymeric carrier has a solubility in water of at least about 0.05 g/mL at 80° C. and 1 atm.

[36.] The present invention also provides for the liquid, aqueous antimicrobial composition of embodiment 35, wherein at least about 90 mol. % of aqueous antimicrobial composition will remain stable at about 20° C. and at about 50% relative humidity, when exposed to the atmosphere, for at least about 9 months.

[37.] The present invention also provides for the liquid, aqueous antimicrobial composition of any one of embodiments 35-36, including less than about 0.1 wt. % organic solvent.

[38.] The present invention also provides for the liquid, aqueous antimicrobial composition of any one of embodiments 35-36, including less than about 0.1 wt. % methanol.

[39.] The present invention also provides for the liquid, aqueous antimicrobial composition of any one of embodiments 35-38, that is relatively non-toxic, such that the $LD_{50}$ in rats is greater than about 2 ml/kg of body mass.

[40.] The present invention also provides for the liquid, aqueous antimicrobial composition of any one of embodiments 35-39, wherein the antimicrobial agent includes at least one of a quaternary ammonium compound, a silver-containing compound, a phenol containing compound, a secondary or tertiary nitrogen containing compound, an aldehyde containing compound, and a peroxygen containing compound.

[41.] The present invention also provides for the liquid, aqueous antimicrobial composition of any one of embodiments 35-40, wherein the antimicrobial agent includes at least one of:

3-(trimethoxysilyl)propyl dimethyl octadecyl ammonium chloride

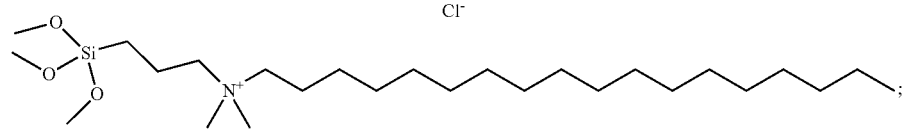 [SMILES: [Cl-] ; CCCCCCCCCCCCCCCCCC[N+](C)(C)CCC[Si](OC)(OC)OC]

poly(hexamethylene biguanide) hydrochloride (PHMB)

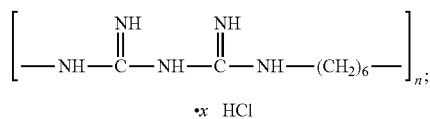

sialic acid (N-acetyl-neuraminic acid, Neu5Ac, NAN, NANA)

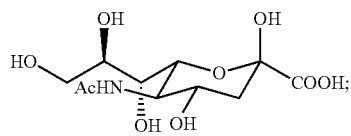 [SMILES: CC(=O)NC1C(O)CC(O)(C(=O)O)OC1[C@H](O)[C@H](O)CO]

poly(diallyldimethylammonium chloride) (poly DADMAC)

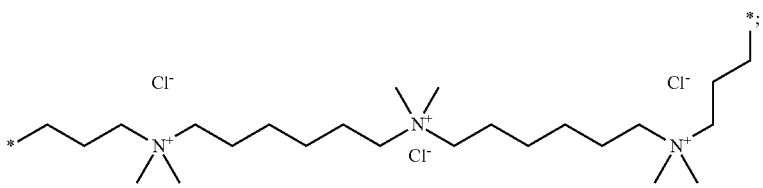

poly(vinyl benzyltrimethyl ammonium chloride) (PVBT-MAC);
5-chloro-2-(2,4-dichlorophenoxy)phenol;
alkyldimethylbenzylammonium chloride (ADBAC);
2,4,4'-trichloro-2'-hydroxydiphenyl ether

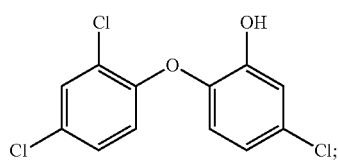 [SMILES: Oc1cc(Cl)ccc1Oc1ccc(Cl)cc1Cl]

methylisothiazolinone

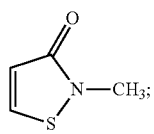

[N-(2-hydroxyl)propyl-3-trimethylammonium chitosan chloride] (HTCC); and
a silver complex of poly(amidoamine) (PAMAM);
2-isopropyl-5-methylphenol; and
poly-D-glucosamine.

[42.] The present invention also provides for the liquid, aqueous antimicrobial composition of any one of embodiments 35-41, wherein the polymeric carrier includes at least one of polyvinyl alcohol (PVA), polyvinyl acetate (PVAc), starch, polyethylene glycol (PEG), ethylene vinyl alcohol (EVA), cellulose, cellulose acetate, and chitosan.

[43.] The present invention also provides for the liquid, aqueous antimicrobial composition of any one of embodiments 35-42, wherein the weight ratio of antimicrobial agent to polymeric carrier is about 1:99 to about 99:1.

[44.] The present invention also provides for the liquid, aqueous antimicrobial composition of any one of embodiments 35-43, which is relatively non-leaching.

[45.] The present invention also provides for the liquid, aqueous antimicrobial composition of any one of embodiments 35-44, further including at least one ($C_1$-$C_{10}$)alkyl substituted with one or more hydroxyl.

[46.] The present invention also provides for the liquid, aqueous antimicrobial composition of any one of embodiments 35-45, which includes less than about 0.1 wt. % heavy metals.

[47.] The present invention also provides for the liquid, aqueous antimicrobial composition of any one of embodiments 35-46, which includes less than about 0.1 wt. % poly-chlorinated phenols (PCPs).

[48.] The present invention also provides for a liquid, aqueous antimicrobial composition including:
(a) an antimicrobial agent including 3-(trimethoxysilyl) propyl dimethyl octadecyl ammonium chloride,
(b) a polymeric carrier including polyvinyl alcohol (PVA),
(c) water,
(d) alcohol, and
(e) fragrance.

[49.] The present invention also provides for a liquid, aqueous antimicrobial composition including:
(a) about 0.01 to about 4.0 wt. % of 3-(trimethoxysilyl) propyl dimethyl octadecyl ammonium chloride,
(b) about 0.1 to about 4.0 wt. % of polyvinyl alcohol (PVA),
(c) about 18 to about 99.9 wt. % water,
(d) 0 to about 80.0 wt. % of ethanol,
(e) 0 to about 2.0 wt. % fragrance, and
(f) 0 to about 0.004 wt. % of an anti-foaming agent.

[50.] The present invention also provides for a liquid, aqueous antimicrobial composition including:
(a) about 0.5 wt. % of 3-(trimethoxysilyl)propyl dimethyl octadecyl ammonium chloride,
(b) about 1.0 wt. % of polyvinyl alcohol (PVA),
(c) about 88.3 wt. % of water,
(d) about 10.0 wt. % of ethanol,
(e) about 0.2 wt. % of fragrance, and
(f) about 0.002 wt. % of an anti-foaming agent.

[51.] The present invention also provides for the antimicrobial composition of any one of embodiments 1-24 and 35-50, wherein the composition is configured for use in a sprayable composition.

[52.] The present invention also provides for the antimicrobial composition of any one of embodiments 1-24 and 35-50, wherein the composition is configured for use in an athletic equipment composition, an athletic gear composition, an athletic apparel composition, or an athletic footwear composition.

[53.] The present invention also provides for the antimicrobial composition of any one of embodiments 1-24 and 35-50, wherein the composition is configured for use in a sprayable athletic equipment composition, a sprayable athletic gear composition, a sprayable athletic apparel composition, or a sprayable athletic footwear composition.

[54.] The present invention also provides for the antimicrobial composition of any one of embodiments 1-24 and 35-50, wherein the composition is configured for use in manufacturing a plastic or rubber composition.

[55.] The present invention also provides for the antimicrobial composition of any one of embodiments 1-24 and 35-50, wherein the composition is configured for use in manufacturing a fabric or textile composition.

[56.] The present invention also provides for a method of reducing the number of microbes located upon a substrate, the method including contacting the substrate with an antimicrobial composition of any one of embodiments 1-24 and 35-50, for a sufficient period of time to reduce the number of microbes located upon the substrate.

[57.] The present invention also provides for a method of killing or inhibiting a microorganism, the method including contacting the microorganism with an antimicrobial composition of any one of embodiments 1-24 and 35-50, for a sufficient period of time to kill or inhibit the microorganism.

[58.] The present invention also provides for a method of eliminating or lowering malodor associated with the growth of a microorganism, the method including contacting the microorganism with an antimicrobial composition of any one of embodiments 1-24 and 35-50, for a sufficient period of time effective to eliminate or lower the malodor.

[59.] The present invention also provides for a method of eliminating or lowering staining or discoloration of a substrate, which is associated with the growth of a microorganism, the method including contacting the substrate with an antimicrobial composition of any one of embodiments 1-24 and 35-50, for a sufficient period of time effective to eliminate or lower the staining or discoloration.

[60.] The present invention also provides for the method of any one of embodiments 56-59, wherein the microbe or microorganism includes at least one of a virus, fungus, mold, slime mold, algae, yeast, mushroom and bacterium.

[61.] The present invention also provides for a substrate having applied thereto a coating or film to provide antimicrobial properties, said coating or film formed from contacting the substrate with an antimicrobial composition of any one of embodiments 1-24 and 35-50.

[62.] The present invention also provides for the substrate of embodiment 61, wherein the contacting includes at least one of spraying, dipping, brushing, and rolling the substrate with the antimicrobial composition.

[63.] The present invention also provides for the substrate of any one of embodiments 61-62, wherein at least about 90 mol. % of the antimicrobial located on the substrate will remain stable on the substrate, at about 20° C. and at about 50% relative humidity, when exposed to the atmosphere, for at least about 3 months.

[64.] The present invention also provides for the substrate of any one of embodiments 61-63, which is at least one of a topical surface of a mammal, non-woven fabric, woven fabric, natural textile, synthetic textile, organic particulate, inorganic particulate, fiber, agglomerate, foam, film, cellulosic material, metal, plastic, natural rubber, synthetic rubber, glass, paint, stain, adhesive, stone, grout, fiberglass, medical device, clothing apparel, sporting equipment, wood, concrete, construction product, building product, and activated carbon.

[65.] The present invention also provides for a kit including:

(a) an enclosed container including a removable closure, (b) an antimicrobial composition of any one of embodiments 1-24 and 35-50, located inside the enclosed container, and (c) printed indicia located on the enclosed container.

[66.] The present invention also provides for the kit of embodiment 65, further including a liquid applicator including at least one of a spray bottle, wipe, cloth, sponge, non-woven fabric, and woven fabric.

The invention will now be described by the following non-limiting examples.

EXAMPLES

Examples 1 and 2

Examples 1 and 2 evaluated the adsorption of TPAC on starch and polyvinyl alcohol (PVA) surfaces.

Example 1

Into a 250 mL round bottomed flask were placed 50 mL of hexanes, 15 mL of 72% TPAC in methanol, and 15 g of soluble starch.

Example 2 into a 250 mL round bottomed flask were placed 50 mL of hexanes, 15 mL of 72% TPAC in methanol, and 10 g of fully hydrolyzed polyvinyl alcohol (mol. wt. 89-90,000).

Each flask was attached to a condenser and stirred vigorously in a water bath at approximately 40° C. for about 1 hour. The samples were then allowed to stir overnight at room temperature (~18 hr.). Each flask was then placed on a rotary evaporator and solvent was removed under vacuum until relatively dry to give a powder. Each powder was then dissolved in water at a concentration of 1 wt %. The dissolution required heating and stirring. Each powder went into solution.

A portion of each clear solution was pipetted into a white weighing dish and sprayed with bromocresol purple to determine the presence of TPAC. The bromocresol purple will complex with the quaternary ammonium portion of the TPAC molecule to show a deep blue color. A failure will show either a yellow, or at high pH, a purple color.

The sample containing polyvinyl alcohol (PVA) showed a color change, but the sample containing starch did not. This indicated that the sample containing polyvinyl alcohol was successfully coated with TPAC while the sample containing starch was not coated with TPAC.

Examples 3, 4, and 5

Examples 3 and 4 evaluated the amount of adsorption of TPAC on PVA (wt/wt) as a function of time and temperature. Samples having the same weight ratios of TPAC to PVA were prepared but allowed to react for various periods of time and temperature.

Example 3

Into a 250 mL round bottomed flask were placed 100 mL of hexanes, 15 mL of 72% TPAC in methanol, and 10 g of fully hydrolyzed polyvinyl alcohol (MW 89-90,000). The sample was stirred for 4 hr at 60° C. The sample was worked up as described in Example 2. The sample was found to have about 3 wt % of TPAC adsorbed onto the PVA powder

Example 4

Into a 250 mL round bottomed flask were placed 50 mL of hexanes, 15 mL of 72% TPAC in methanol, and 10 g of fully hydrolyzed polyvinyl alcohol (MW 89-90,000). The sample was stirred for 18 hr at room temperature. The sample was worked up as described in Example 2. The sample was found to have about 10 wt % of TPAC adsorbed onto the PVA powder

Example 5

Into a 250 mL round bottomed flask were placed 50 mL of hexanes, 15 mL of 72% DC5700 in methanol, and 10 g of fully hydrolyzed polyvinyl alcohol (MW 89-90,000). The sample was stirred for 4 days at room temperature. The sample was worked up as described in Example 2. The sample was found to have about 10 wt % of TPAC adsorbed onto PVA powder Examples 6, 7, and 8

The following examples demonstrate the use of other solvents to determine how they affect the adsorption of TPAC onto PVA powder Example 6

A sample was prepared in a manner similar to that described in Example 2 above. The sample contained 15 mL 72% TPAC; 10 g of fully hydrolyzed PVA (MW 89-90,000); and 50 mL of 1,2-methoxypropanol. The sample was stirred at room temperature for 18 hours.

Example 7

A sample was prepared in a manner similar to that described in Example 2 above. The sample contained 15 mL 72% TPAC; 10 g of fully hydrolyzed PVA (MW 89-90,000); 1.08 g of deionized water and 50 mL of 1,2-methoxypropanol. The sample was prepared by first adding solvent, followed by water, then TPAC. These were stirred for 20 minutes prior to adding the PVA. The sample was stirred at room temperature for 18 hours.

Example 8

A sample was prepared in a manner similar to that described in Example 1 above. The sample contained 45 mL 72% TPAC; 10 g of fully hydrolyzed PVA (MW 89-90,000); and 50 mL of hexanes. The sample was stirred at room temperature for 18 hours.

Samples prepared in Examples 6, 7, and 8 were evaluated to determine the amount of TPAC adsorbed onto the polyvinyl alcohol. The samples from Examples 6 and 7 showed less adsorption onto PVA than those of Examples 1 and 2 above. The sample prepared in Example 7 showed an increase in adsorption from 10% to 12%.

Examples 9 and 10

The following Examples demonstrate the use of ground PVA powders to prepare antimicrobial powders. PVA powders were ground for 5 min. in a coffee grinder to decrease the particle size and increase the available surface area.

Example 9

Into a 250 mL round bottomed flask were placed 50 mL of hexanes, 15 mL of 72% TPAC in methanol, and 10 g of ground fully hydrolyzed polyvinyl alcohol (MW 89-90,000).

Example 10

Into a 250 mL round bottomed flask were placed 50 mL of hexanes, 15 mL of 72% DC5700 in methanol, and 10 g of ground partially hydrolyzed polyvinyl alcohol (MW ~31,000).

Samples from Examples 9 and 10 were evaluated as described above. The sample from Example 9 showed an adsorption of less than 0.3 g/g TPAC/PVA. The sample from Example 10 showed an adsorption of about 6% g/g, had some solubility in methanol, but did not filter well. The partially hydrolyzed PVA swelled in some solvents (i.e., methanol), so a nice dry powder could not be achieved.

Examples 11 and 12

Example 11

Into a 250 mL round bottomed flask were placed 50 mL of hexanes, followed by addition of 27 mL of 72% TPAC in methanol via syringe. 25 g of fully hydrolyzed polyvinyl alcohol (MW 89-90,000) was then added with vigorous stirring. Upon dissolution, the flask was placed on a rotary evaporator to remove the methanol and hexanes. As the solvent was removed, a powder formed.

A portion of the powder 2 wt % was added to a solution of water and heated at about 80° C. to form a clear 2 wt % solution. The solution was then evaluated as described above to determine the content of TPAC. The sample was found to have 0.94% DC5700, indicating the dry powder is nearly 1/1 (g/g) TPAC/PVA.

Example 12

Example 11 was scaled up several times. The samples were placed in glass baking pans and dried in a vacuum oven and then air dried. Samples were evaluated by preparing a 2 wt % solution in deionized water, heating to form a clear solution.

Samples were found to contain a ratio of TPAC to PVA ranging from of about 0.05/1 to 1.75/1.

Example 12-01

1.5 g of Thymol (2-isopropyl-5-methylphenol) was dissolved in 50 mL of ethyl alcohol in a 250 mL round bottom flask. 30 g of fully hydrolyzed polyvinyl alcohol (MW 89,000-90,000) was added to the flask with vigorous stirring. The flask was subsequently placed on a rotary evaporator to remove all ethyl alcohol and create a fine, uniform powder. A clear aqueous solution of ~0.05 wt % Thymol (1.05 wt % resulting powder) was made from this powder by dissolving at ~80° C. Similar solutions with up to 10% alcohol were also stable and clear.

Example 12-02

Similarly to example 12-01, 3.0 g of Thymol was dissolved in 50-60 mL of ethyl alcohol, then 30 g of PVA was added with stirring, and the ethyl alcohol was pulled off via rotary evaporator. The resulting fine, white powder was dissolved in water at ~80° C. at 0.1 wt % Thymol (1.1 wt % resulting powder) to create a clear solution. Both examples 12-01 and 12-02 were dried onto polycarbonate squares to form clear films.

Example 12-03

A uniform powder was made similarly to examples 12-01 and 12-02. In a 250 mL round bottom flask, 3 g of benzalkonium chloride (alkyldimethylbenzylammonium chloride) was dissolved in 50-60 mL of ethyl alcohol. 30 g of PVA was added with stirring, and then the flask was placed on a rotary evaporator to pull off all of the ethyl alcohol and form a powder.

Example 12-04

A uniform powder was made similarly to examples 12.03. In a 250 mL round bottom flask, 9 g of benzalkonium chloride (alkyldimethylbenzylammonium chloride) was dissolved in 50-60 mL of ethyl alcohol. 30 g of PVA was added with stirring, and then the flask was placed on a rotary evaporator to pull off all of the ethyl alcohol and form a powder. Both examples 12-03 and 12-04 were dissolved in water at ~80° C. to form clear solutions (1.1 wt % powder and 1.3 wt % powder respectively). Solutions contained from 0-10 wt % added ethyl alcohol. Solutions were also dried onto polycarbonate squares to create clear films.

Example 12-05

3.9 g of Alkyldimethylbenzy ammonium chloride and 20.8 g of 72% TPAC were dissolved in 60-80 mL of ethanol. 30 g of fully hydrolyzed PVA was added with stirring to form a slurry. The flask was then placed on a rotary evaporator to pull oft (via vacuum) the ethanol. The result was dried further in a vacuum oven to obtain a dry, white, uniform powder of small granules. This powder was then dissolved into water at ~80° C. and coated on polycarbonate carriers for residual antimicrobial testing. Furthermore, 0-15% alcohol was added to the solutions and antimicrobial spray testing was performed.

Results

Examples 12-01 to 12-05

Solutions of examples 12-01 to 12-05 were used to coat polycarbonate or glass carriers. Once dried, bacteria were inoculated on top of the coating and a log reduction of bacteria was obtained after a certain contact time. CFU=Colony Forming Units, TNTC=Too numerous to count, BCP=benzalkonium chloride powder, ThP=thymol powder

| Sample | Organism | # of CFU recovered | | | Positive Controls | Avg. total number of CFU inoculated |
|---|---|---|---|---|---|---|
| | | 10 min | 30 min | 60 min | | |
| 1.3 wt % Benzalkonium Powder Example(12-04) | SA SA PA PA | 0 0 0 0 | 1 0 0 0 | 0 0 0 0 | *Staph. aureus* *Psued. aeruginosa* | 530 1200 |
| 1.1 wt % thymol Powder Example(12-02) | SA SA PA PA | TNTC TNTC TNTC 270 | ~300 ~300 11 12 | 89 0 1 n/a | | |

Test Samples (1 hr. contact time)

| Sample | Total # of CFU Recovered | | Positive Controls | Avg. total number of CFU inoculated |
|---|---|---|---|---|
| | *Staph. aureus* | *Psued. Aeruginosa* | | |
| 1.1 wt % BCP | 0 0 | 0 0 | Staph. aureus Psued. Aeruginosa | 1700 15000 |
| 1.3 wt % BCP | 0 0 | TNTC 0 | | |
| 1.05 wt % ThP | 80 0 | 0 5 | | |
| 1.1 wt % ThP | 45 0 | 0 145 | | |
| 0.05 wt % Chitosan, 1 wt % PVA | 485 2.5 | 25 10 | | |
| 0.1 wt % Chitosan, 1 wt% PVA | n/a 30 | 5 30 | | |

*Staphylococcus aureus*

| Sample | # of CFU inoculated | CFU Recovered | | |
|---|---|---|---|---|
| | | 1 min | 5 min | 10 min |
| 1.3 wt % BCP (Example 12-04) | 200000 200000 200000 200000 | 0 0 11 0 | 0 0 0 0 | 0 0 0 0 |

| Sample | 10 minute contact time | | |
|---|---|---|---|
| | Average CFU inoculated | # CFU Recovered | Average Log 10 Reduction |
| 1 wt % PVA control | $5.95 \times 10^6$ | TNTC TNTC 112 TNTC TNTC | None |

-continued

| | | 126 | |
| --- | --- | --- | --- |
| | | TNTC | |
| | | TNTC | |
| | | N/A | |
| 0.3 wt % benzalkonium chloride control | $1.8 \times 10^6$ | TNTC >300-appx. 360 | 0.5 |
| | $2.0 \times 10^6$ | TNTC >300-appx. 400 | |
| | $1.9 \times 10^6$ | TNTC >300-appx. 375 | |
| 1.3 wt % BCP (Example 12-04) | $2.05 \times 10^5$ | >300-appx. 350 45 | 2.88 |
| | $5.0 \times 10^3$ | 10 1 | |
| | $5.0 \times 10^2$ | 10 2 0 | |

A film formed on polycarbonate surfaces from a 1.5% solution of powder, Example 12 (TPAC/PVA=0.5/1), was used to obtain the results below.

| | Sample | CFU Inoculated | CFU Recovered | Log Reduction |
| --- | --- | --- | --- | --- |
| *Pseudomonas aeruginosa* | | | | |
| 30 minutes | A | 1700 | 1255 | 0.13 |
| | B | 1700 | 1210 | 0.15 |
| | C | 1700 | 1155 | 0.17 |
| 60 minutes | A | 1700 | 965 | 0.25 |
| | B | 1700 | 1050 | 0.21 |
| | C | 1700 | 1160 | 0.17 |
| *Staphylococcus aureus* | | | | |
| 30 minutes | A | 2060 | 1455 | 0.15 |
| | B | 2060 | 680 | 0.48 |
| | C | 2060 | 1085 | 0.28 |
| 60 minutes | A | 2060 | N/A | N/A |
| | B | 2060 | 0 | 3.31 |
| | C | 2060 | 64 | 1.51 |
| *Candida albicans* | | | | |
| 30 minutes | A | 1700 | 20 | 1.93 |
| | B | 1700 | 0 | 3.23 |
| | C | 1700 | 445 | 0.58 |
| 60 minutes | A | 1700 | 0 | 3.23 |
| | B | 1700 | 10 | 2.23 |
| | C | 1700 | 0 | 3.23 |
| *Brevibacterium epidermidis* | | | | |
| 30 minutes | A | 1330 | 120 | 1.04 |
| | B | 1330 | 15 | 1.95 |
| | C | 1330 | 0 | 3.12 |
| 60 minutes | A | 1330 | 0 | 3.12 |
| | B | 1330 | 5 | 2.42 |
| | C | 1330 | 0 | 3.12 |
| *Staphylococcus epidermidis* | | | | |
| 30 minutes | A | 1220 | 20 | 1.79 |
| | B | 1220 | 25 | 1.69 |
| | C | 1220 | 60 | 1.31 |
| 60 minutes | A | 1220 | 0 | 3.09 |
| | B | 1220 | 5 | 2.39 |
| | C | 1220 | 0 | 3.09 |

| Test Substance | Contact time | Sample | CFU Inoculated | CFU Recovered | Average Log Reduction |
| --- | --- | --- | --- | --- | --- |
| 0.5% TPAC, 0.13% BZK, 1% PVA | 5 minutes | A | 6.00E+05 | 9 | 3.87 |
| | | B | | 35 | |
| | | C | | 17 | |
| | 10 minutes | A | 5.10E+05 | 0 | 5.58 |
| | | B | | 1 | |
| | | C | | 0 | |
| 0.13% BZK, 1% PVA | 5 minutes | A | 6.00E+05 | 0 | 5.78 |
| | | B | | 0 | |
| | | C | | 0 | |
| | 10 minutes | A | 5.10E+05 | 0 | 5.71 |
| | | B | | 0 | |
| | | C | | 0 | |
| 0.5% TPAC, 0.3% BZK, 1% PVA | 5 minutes | A | 6.00E+05 | 0 | 5.78 |
| | | B | | 0 | |
| | | C | | 0 | |
| | 10 minutes | A | 5.10E+05 | 0 | 5.71 |
| | | B | | 0 | |
| | | C | | 0 | |
| 0.13% BZK, 1% PVA | 5 minutes | A | 6.00E+05 | 0 | 5.78 |
| | | B | | 0 | |
| | | C | | 0 | |
| | 10 minutes | A | 5.10E+05 | 0 | 5.71 |
| | | B | | 0 | |
| | | C | | 0 | |
| 0.5% TPAC, 1% PVA | 5 minutes | A | 6.00E+05 | TNTC | N/A |
| | | B | | TNTC | |
| | 10 minutes | A | 5.10E+05 | TNTC | N/A |
| | | B | | TNTC | |

Test substances are described as wt % chemical of solution, with which films were made on polycarbonate surfaces. The bacteria were then inoculated on the dried carriers to obtain the results above,

| Test Organism | Contact time | Sample | CFU Inoculated | (+/0) |
| --- | --- | --- | --- | --- |
| *E. coli* | 3 minutes | 1 | 2.50E+03 | 0 |
| | | 2 | | 0 |
| | | 3 | | 0 |
| | | 4 | | 0 |
| | | 5 | | 0 |
| | 5 minutes | 1 | 2.50E+03 | 0 |
| | | 2 | | 0 |
| | | 3 | | 0 |
| | | 4 | | 0 |
| | | 5 | | 0 |
| *C. albicans* | 3 minutes | 1 | 1.30E+03 | 0 |
| | | 2 | | 0 |
| | | 3 | | 0 |
| | | 4 | | 0 |
| | | 5 | | 0 |
| | 6 minutes | 1 | 1.30E+03 | 0 |
| | | 2 | | (+) |
| | | 3 | | 0 |
| | | 4 | | 0 |
| | | 5 | | 0 |
| *M. terrae* | 5 minutes | 1 | 8.40E+05 | 0 |
| | | 2 | | 0 |
| | | 3 | | 0 |

-continued

| Test Organism | Contact time | Sample | CFU Inoculated | (+/0) |
|---|---|---|---|---|
| | | 4 | | 0 |
| | | 5 | | 0 |
| | 10 minutes | 1 | 8.40E+05 | 0 |
| | | 2 | | 0 |
| | | 3 | | 0 |
| | | 4 | | 0 |
| | | 5 | | 0 |

Note:
"+" indicates growth, "0" indicates no growth
Test substance used: 1% PVA, 0.5% TPAC, 0.13% BAC, 15% ethanol
The table above illustrates the efficacy of a certain solution created from example 12-05. Bacteria were inoculated on the carriers, then the solution was sprayed and allowed to sit for the indicated contact time.

| Jan. 27, 2012 Germicidal Spray Test | | | | | | |
|---|---|---|---|---|---|---|
| Test | S. aureus | | P. aeruginosa | | S. enterica | |
| sample | 5 min | 10 min | 5 min | 10 min | 5 min | 10 min |
| 1 A | 0 | 0 | 0 | 0 | 0 | 0 |
| B | 0 | 0 | 0 | 0 | 0 | 0 |
| C | 0 | 0 | 0 | 0 | 0 | 0 |
| 2 A | + | + | 0 | 0 | 0 | 0 |
| B | + | + | 0 | 0 | 0 | 0 |
| C | + | 0 | 0 | 0 | 0 | 0 |
| 3 A | + | + | 0 | 0 | 0 | 0 |
| B | + | 0 | 0 | 0 | 0 | 0 |
| C | + | + | 0 | 0 | 0 | 0 |
| 4 A | + | + | 0 | 0 | 0 | 0 |
| B | + | + | 0 | + | 0 | 0 |

NOTE:
+ means survivors were present, and 0 represents total kill.

Test Articles Used

| Test articles | |
|---|---|
| 1 | 1% PVA-0.5% TPAC-15% EtOH-0.13% BAC |
| 2 | 1% PVA-0.5% TPAC-15% EtOH-0.07% BAC |
| 3 | 1% PVA-0.5% TPAC-10% EtOH-0.13% BAC |
| 4 | 1% PVA-0.5% TPAC-10% EtOH |

Positive Controls

| Positive Controls—Inoculum Titer (CFU) | |
|---|---|
| SA | 3.75E+06 |
| PA | 2.48E+06 |
| SE | 4.50E+04 |

The three tables above represent another liquid spray test in which the bacteria were inoculated on carriers, sprayed with the solution, then allowed to sit for the indicated contact times.

Example 13

The powder prepared in Example 4 was used to prepare a solution of 352 g of deionized water; 8 g of TPAC coated PVA (0.1 g/1 g) and 40 g of isopropyl alcohol. The solution was clear and contained 0.21% TPAC.

This solution was used to soak 12 polycarbonate 1 inch×1 inch (2.5 cm×2.5 cm) squares for approximately 4 hours. The coated squares were then placed in Petri dishes to dry overnight. These squares were then used for the *Staphylococcus aureus* residual test. After a period of 30 minutes, a greater than 99% reduction of bacteria was seen on the coated polycarbonate squares when compared to an uncoated control.

Example 14

A solution similar to that of Example 13 was prepared. This solution was used to coat 3 inch×3 inch (7.6 cm×7.6 cm) cotton squares. The cotton squares were soaked in a shallow dish for approximately 18 hrs. The excess solution was poured off, and the trays were placed in an oven for 4 hrs at 60° C. The coated cotton, along with uncoated controls were tested against *Staphylococcus aureus* with a contact time of 30 and 60 minutes. After both time points, a greater than 99% reduction of bacteria was seen on the coated cotton squares compared to an uncoated control.

Example 15

Evaluation of Samples

Each fabric sample was treated with product applied by spraying 1 ounce of product onto the fabric thoroughly or submerging the fabric sample in each formulation for a period of five minutes, and allowing the sample to dry for 24 hours. All tests were performed under controlled parameters (i.e., humidity, temperature, etc.) using artificial perspiration obtained from the American Association of Textile Chemists and Colorists (AATCC) test method 15. The absorption test followed the AATCC test method 79 protocol; all other studies were independently constructed.

Fluid Dispersion Test

The Fluid Dispersion Test is designed to measure the fluid dispersion (i.e., wicking) properties of moisture wicking performance apparel. Due to the construction of the fabric of moisture wicking products, testing required the fabric to remain flat throughout the testing process; within the fabric there exist horizontal channels that allow fluid to wick more rapidly towards the perimeter. A diameter of 6 cm was set within the sample. A burette was used to deliver the artificial perspiration to the center of the fabric sample until enough volume of fluid was applied for the fabric to disperse across the premeasured diameter both horizontally and vertically. When saturated with artificial perspiration fluid, the originally white moisture wicking fabric appears transparent and darkens in color. The volume of artificial perspiration fluid to saturate the fabric was recorded. The ability of the fabric to disperse artificial perspiration was evaluated in comparison with a control sample and other product samples.

Moisture Evaporation Test

The Moisture Evaporation test is designed to analyze the time required for samples saturated with artificial perspiration to evaporate fluid to the point where discoloration of the fabric can no longer be seen. This test analyzes the time required for moisture wicking fabrics to evaporate fluid. The experiment was setup with the fabric samples submerged in artificial perspiration for 30 seconds; samples were then immediately removed and placed on a level rack to evaluate the evaporation of fluid. The point at which samples are deemed completely evaporated is when no saturated channel can be seen. All samples were examined under atmospheric conditions at room temperature and ambient humidity. Although the humidity fluctuates during testing it all samples are exposed to the same humidity during testing.

Simulated Perspiration Test

The simulated perspiration test evaluates the three stages of wicking; drawing moisture from the skin, dispersing it throughout the fabric to the outer surface of the fabric, and evaporating the moisture from the outer surface of the fabric to cool the wearer. The test provides insight on antimicrobial agents and the impact they have on each phase of wicking. Because the percent influence for each stage on wicking cannot be determined this test provides a feasible and useful analysis of the total wicking performance for each fabric sample and can be used to evaluate the wicking performance of apparel regardless of material.

The Simulated Perspiration Test emulates moisture wicking performance of apparel in direct contact with a moisture source, thus accurately summarizing all three stages of the wicking process accurately. Grouting sponges were selected as the moisture release agent for their small pore size and high water holding capacity. Sponges were cut into a 5.5 inch diameter, having a thickness of 2.4 inches, and placed inside a 5.5 inch diameter container that is 2.25 inches tall. With the sponge saturated with artificial perspiration, the sponge was set inside the container and additional artificial perspiration fluid is added to have all samples equivalent in mass; the fabric samples are included in the mass. The container including fabric sample, sponge within the container, and artificial perspiration were monitored for 24 hours. With the fabric sample completely covering and contacting the sponge, all loss in mass was attributed to fluid loss evaporated through the fabric. The loss in mass can be used to measure the rate at which each fabric sample wicks moisture from the surface of the sponge.

What is claimed is:

1. A method of eliminating or lowering malodor associated with a microorganism, the method comprising contacting the microorganism with a liquid, aqueous antimicrobial composition comprising:
   (a) about 0.01 to about 4.0 wt. % of 3-(trimethoxysilyl)propyl dimethyl octadecyl ammonium chloride,
   (b) about 0.1 to about 4.0 wt. % of polyvinyl alcohol (PVA),
   (c) about 18 to about 99.9 wt. % water,
   (d) 0 to about 80.0 wt. % of ethanol,
   (e) 0 to about 2.0 wt. % fragrance, and
   (f) 0 to about 0.004 wt. % of an anti-foaming agent
which comprises less than 0.1 wt. % of undissolved solid particulates,
for a sufficient period of time effective to eliminate or lower the malodor;
   wherein at least 95 mol. % of the 3-(trimethoxysilyl)propyl dimethyl octadecyl ammonium chloride is complexed with the polyvinyl alcohol (PVA).

2. A method of eliminating or lowering malodor associated with a microorganism, the method comprising contacting the microorganism with a liquid, aqueous antimicrobial composition comprising:
   (a) about 0.5 wt. % of 3-(trimethoxysilyl)propyl dimethyl octadecyl ammonium chloride,
   (b) about 1.0 wt. % of polyvinyl alcohol (PVA),
   (c) about 88.3 wt. % of water,
   (d) about 10.0 wt. % of ethanol,
   (e) about 0.2 wt. % fragrance, and
   (f) about 0.002 wt. % of an anti-foaming agent
which comprises less than 0.1 wt. % of undissolved solid particulates,
for a sufficient period of time effective to eliminate or lower the malodor;
   wherein at least 95 mol. % of the 3-(trimethoxysilyl)propyl dimethyl octadecyl ammonium chloride is complexed with the polyvinyl alcohol (PVA).

3. The method of claim 1 or 2, wherein the microbe or microorganism is selected from the group consisting of a virus, fungus, mold, slime mold, algae, yeast, mushroom and bacterium.

4. The method of claim 1 or 2, wherein the liquid, aqueous antimicrobial composition is applied to a substrate by at least one of spraying, dipping, brushing, and rolling the substrate with the antimicrobial composition.

5. The method of claim 1 or 2, wherein the liquid, aqueous antimicrobial composition is formulated such that at least 90 mol. % of the antimicrobial located on the substrate will remain stable on the substrate, at 20° C. and at 50% relative humidity, when exposed to the atmosphere, for at least 3 months.

6. The method of claim 1 or 2, wherein the liquid, aqueous antimicrobial composition is applied to a substrate with a liquid applicator comprising at least one of a spray bottle, wipe, cloth, sponge, non-woven fabric, and woven fabric.

7. The method of claim 1 or 2, wherein the liquid, aqueous antimicrobial composition is formulated such that at least 90 mol. % of aqueous antimicrobial composition will remain stable at 20° C. and at 50% relative humidity, when exposed to the atmosphere, for at least 9 months.

8. The method of claim 1 or 2, wherein the liquid, aqueous antimicrobial composition comprises less than 0.1 wt. % methanol.

9. The method of claim 1 or 2, wherein the liquid, aqueous antimicrobial composition is non-toxic, such that the $LD_{50}$ in rats is greater than 2 ml/kg of body mass.

10. The method of claim 1 or 2, wherein the liquid, aqueous antimicrobial composition comprises less than 0.1 wt. % heavy metals.

11. The method of claim 1 or 2, wherein the liquid, aqueous antimicrobial composition comprises less than 0.1 wt. % poly-chlorinated phenols (PCPs).

12. The method of claim 1 or 2, wherein the liquid, aqueous antimicrobial composition is a sprayable composition.

13. The method of claim 1 or 2, wherein the liquid, aqueous antimicrobial composition is applied to a substrate selected from the group consisting of athletic equipment, athletic gear, athletic apparel, and athletic footwear.

14. The method of claim 1 or 2, wherein the liquid, aqueous antimicrobial composition is applied to a topical surface of at least one of a mammal, non-woven fabric, woven fabric, natural textile, synthetic textile, organic particulate, inorganic particulate, fiber, agglomerate, foam, film, cellulosic material, metal, plastic, natural rubber, synthetic rubber, glass, paint, stain, adhesive, stone, grout, fiberglass, medical device, clothing apparel, sporting equipment, wood, concrete, construction product, building product, and activated carbon.

15. The method of claim 1 or 2, wherein the liquid, aqueous antimicrobial composition is applied to a topical surface of at least one of polyester fabric, synthetic polyester fabric, non-engineered polyester fabric, performance apparel, moisture wicking performance fabric, delicate moisture wicking performance fabric, and moisture wicking performance apparel.

16. The method of claim 1 or 2, wherein a substrate is treated one or more times with the liquid, aqueous antimicrobial composition.

17. The method of claim 1 or 2, wherein a substrate is treated one or more times with the liquid, aqueous antimicrobial composition, to provide a coating or film on the substrate, and the resulting film or coating remains stable and retains the antimicrobial properties for at least 1 year.

18. The method of claim 1 or 2, wherein a substrate is treated one or more times with the liquid, aqueous antimicrobial composition, to provide a coating or film on the substrate, and the resulting film or coating remains stable and retains the antimicrobial properties for 1 to 5 years.

* * * * *